(12) United States Patent
Bechhoefer

(10) Patent No.: US 6,728,658 B1
(45) Date of Patent: Apr. 27, 2004

(54) METHOD AND APPARATUS FOR DETERMINING THE HEALTH OF A COMPONENT USING CONDITION INDICATORS

(75) Inventor: Eric Robert Bechhoefer, New Haven, VT (US)

(73) Assignee: Simmonds Precision Products, Inc., Vergennes, VT (US)

( * ) Notice: Subject to any disclaimer, the term of this patent is extended or adjusted under 35 U.S.C. 154(b) by 69 days.

(21) Appl. No.: 10/011,787

(22) Filed: Dec. 4, 2001

Related U.S. Application Data
(60) Provisional application No. 60/293,331, filed on May 24, 2001.

(51) Int. Cl.$^7$ .............................................. G06F 19/00
(52) U.S. Cl. ....................................... 702/181; 702/183
(58) Field of Search ................................ 702/181–185, 702/33–36, 56, 81, 113–115, 117, 119, 187, 188, FOR 123–FOR 126, FOR 134–FOR 137, FOR 139, FOR 426, FOR 171, FOR 172; 706/904–906, 916, 912–914; 703/6–8; 700/51, 109, 110, 175; 701/29, 30; 73/35.09, 570, 802; 340/674, 680, 682, 683

(56) References Cited

U.S. PATENT DOCUMENTS

| | | | | |
|---|---|---|---|---|
| 5,465,321 A | * | 11/1995 | Smyth | 706/20 |
| 5,710,723 A | * | 1/1998 | Hoth et al. | 702/181 |
| 6,014,652 A | | 1/2000 | Hill et al. | 706/16 |
| 6,041,287 A | * | 3/2000 | Dister et al. | 702/182 |
| 6,574,613 B1 | * | 6/2003 | Moreno-Barragan | 706/16 |

FOREIGN PATENT DOCUMENTS

| | | |
|---|---|---|
| DE | 42 07 728 A1 | 9/1993 |
| WO | WO 99/54703 | 10/1999 |

OTHER PUBLICATIONS

Jarque–bera test of normality: Judge, G. G., R.C. Hill, W.E., Griffiths, H. Lutkepohl, and T.–C. Lee. "Introduction to the Theory and Practice of Econometrics", New York, Wiley, pp. 890–893,914–917, (no date).
Lilliefors test of normality: Conover, W.J., "Practical Nonparametric Statistics", New York, Wiley, 1980, pp. 306–359, 360–363,410–413, (no month).
Chi squared: Sheskin, D.J., "Handbook of Parametric and Nonparametric Statistical Procedures", CRC Press, Boca Raton, FL, 1997, pp. 97–112, (no month).
Fukunaga, Keinosuke, Academic Press, "Hypothesis Testing", Introduction to Statistical Pattern Recognition, 51–97, 1990,(no month).
VanTress, Harry, John Wiley & Sons, Inc., "The General Gaussian Problem", Detection, Estimation and Modulation Theory, Part 1, 96–117, 1968. (no month).
Mendenhall, Wackerly and Scheaffer, "The Chi–Square Test", Mathematical Statistics with Application, 642–647, 1990, (no month).

(List continued on next page.)

*Primary Examiner*—Hal Wachsman
(74) *Attorney, Agent, or Firm*—Choate, Hall & Stewart

(57) ABSTRACT

Disclosed are techniques used in connection with determining a health indicator (HI) of a component, such as that of an aircraft component. The HI is determined using condition indicators (CIs) which parameterize characteristics about a component minimizing possibility of a false alarm. Different algorithms are disclosed which may be used in determining one or more CIs. The HI may be determined using a normalized CI value. Techniques are also described in connection with selecting particular CIs that provide for maximizing separation between HI classifications. Given a particular HI at a point in time for a component, techniques are described for predicting a future state or health of the component using the Kalman filter. Techniques are described for estimating data values as an alternative to performing data acquisitions, as may be used when there is no pre-existing data.

18 Claims, 26 Drawing Sheets

OTHER PUBLICATIONS

Smith, J. Derek, Marcel Dekker, Inc., "Causes of Noise", Gear Noise and Vibration, p 2,3–4,52–63 1999, (no month).

Hochmann, et al., "Mechanics of Gear Tooth Crack Signals and their Detection in Application for a Helicopter Health Usage and Management System (HUMS)", Goodrich Company, 1–12, 2002, (no month).

"Eigenvalues and Eigenvectors", 244–253, (no date).

Numerical Recipes In C: The Art of Scietific Computing, "14.3 Are Two Distributions Different?" by Cambridge University Press, 1988–1992, pp. 620–628, (no month).

Mitchell, John, Introduction to Machinery Analysis and Monitoring $2^{nd}$ Edition, "Analyzing Machine Condition––General Characteristics", Pennwell Books, 1993, pp. 171–255, (no month).

* cited by examiner

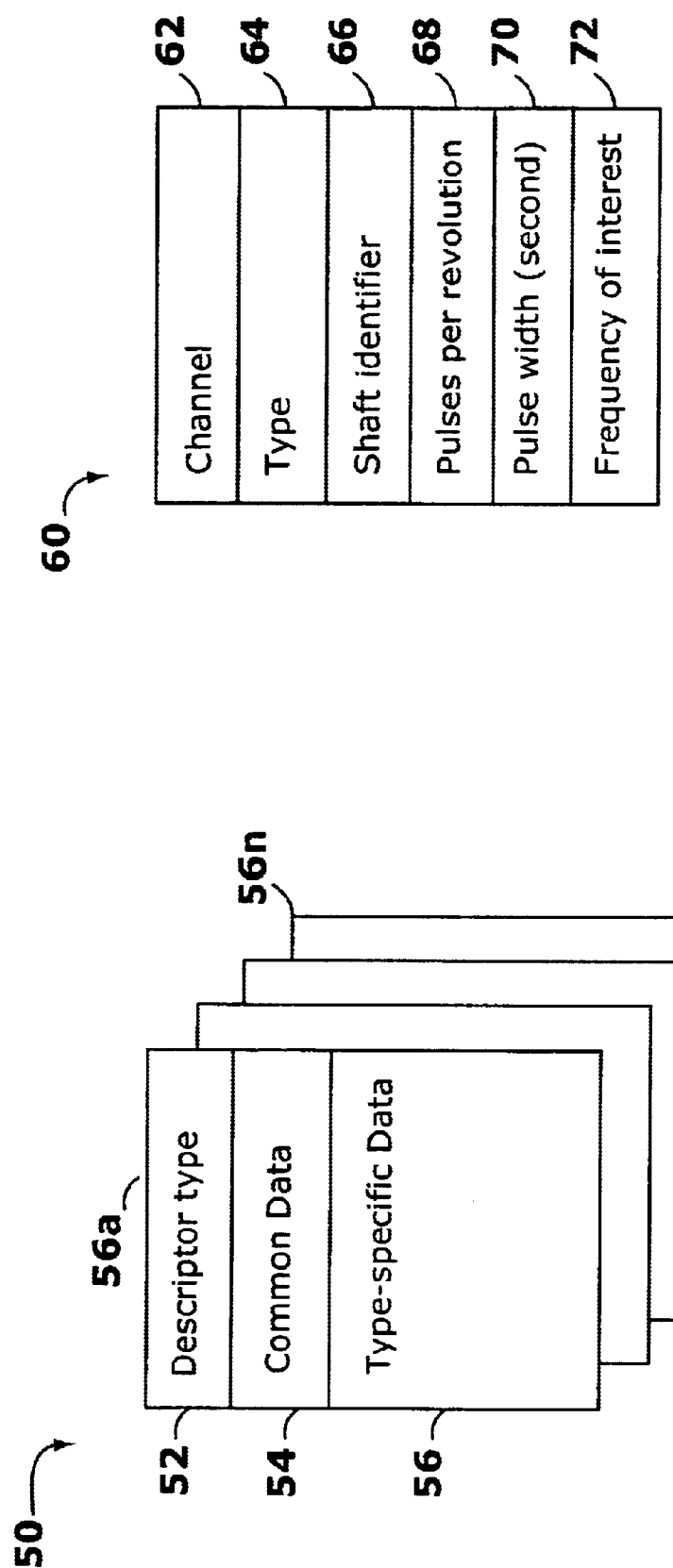

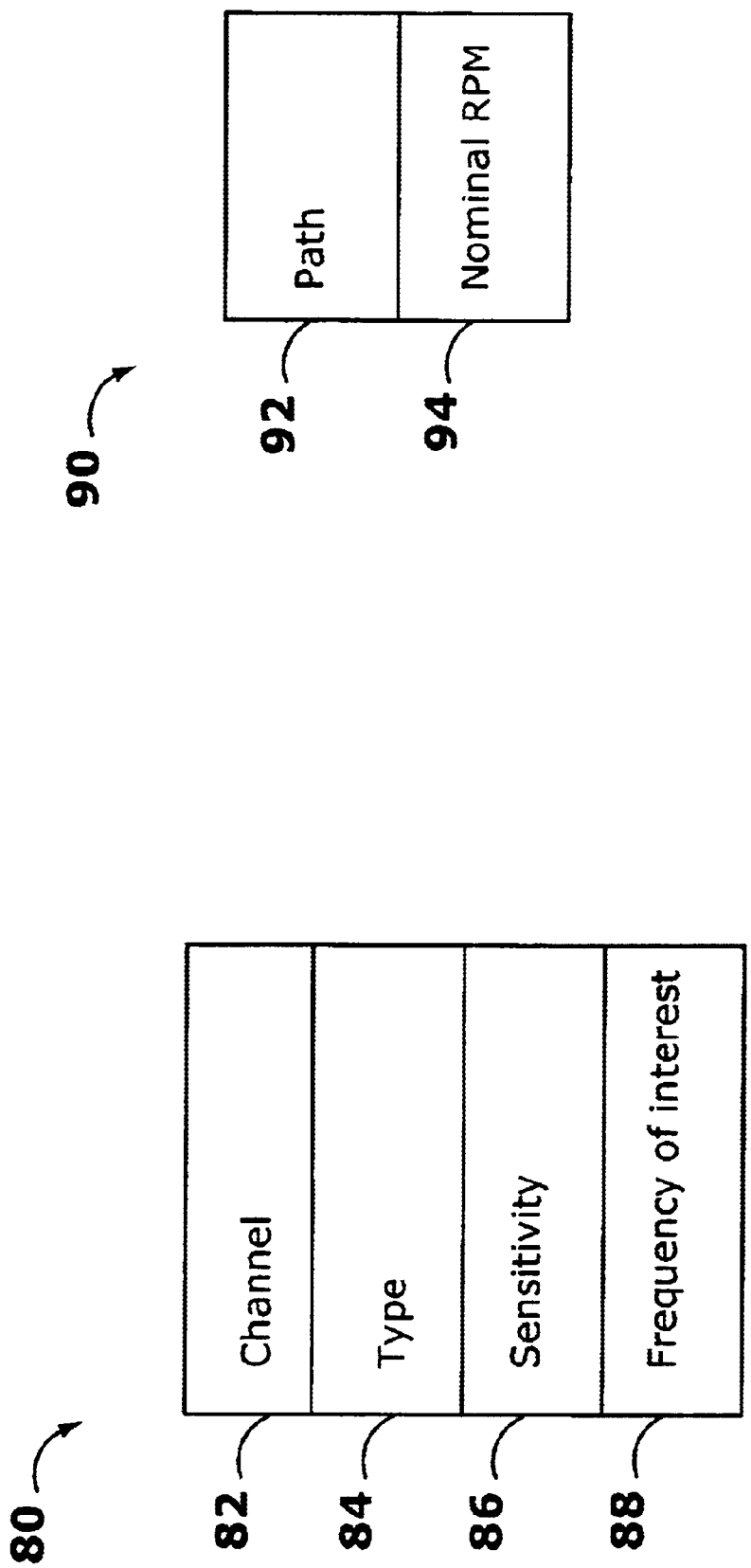

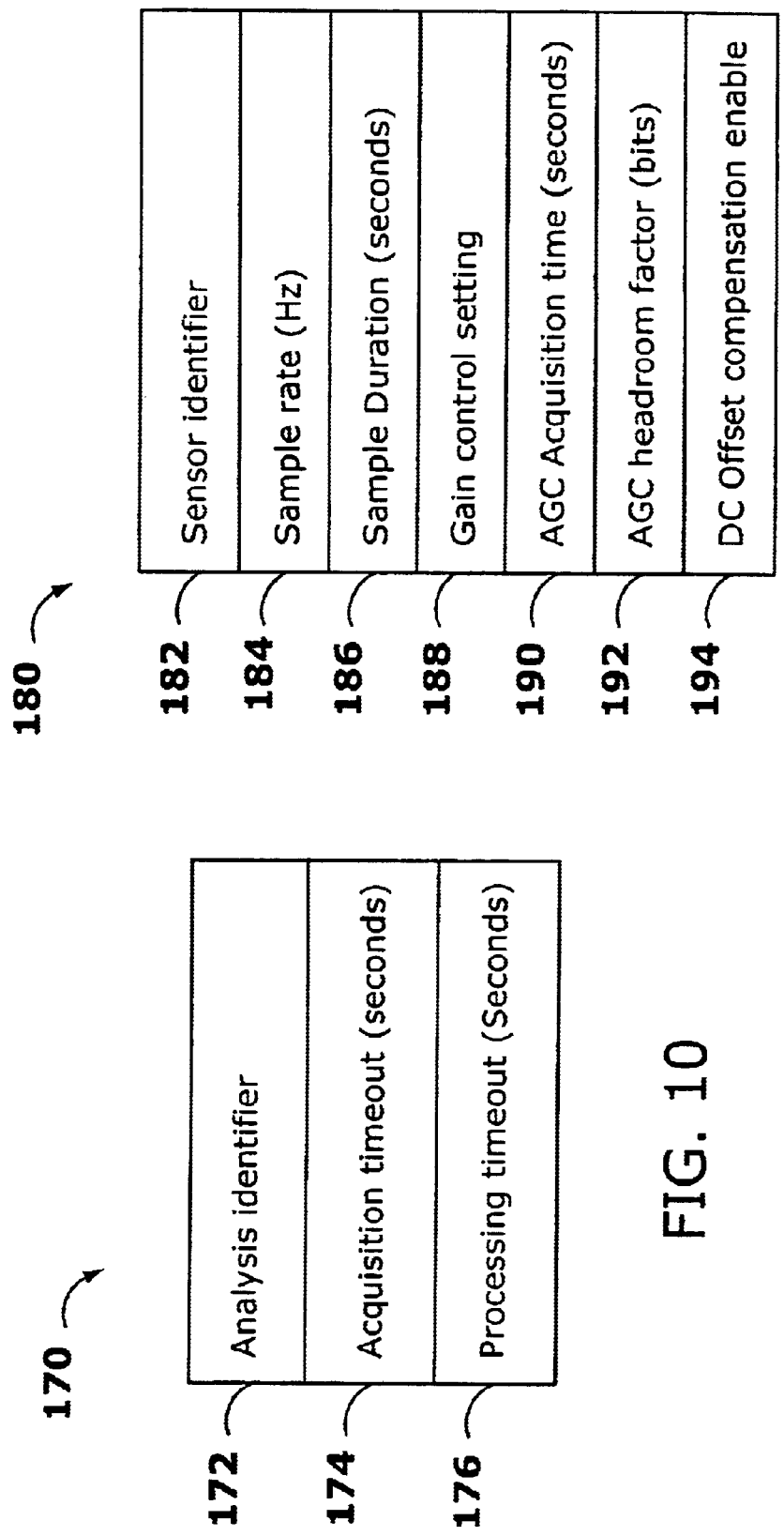

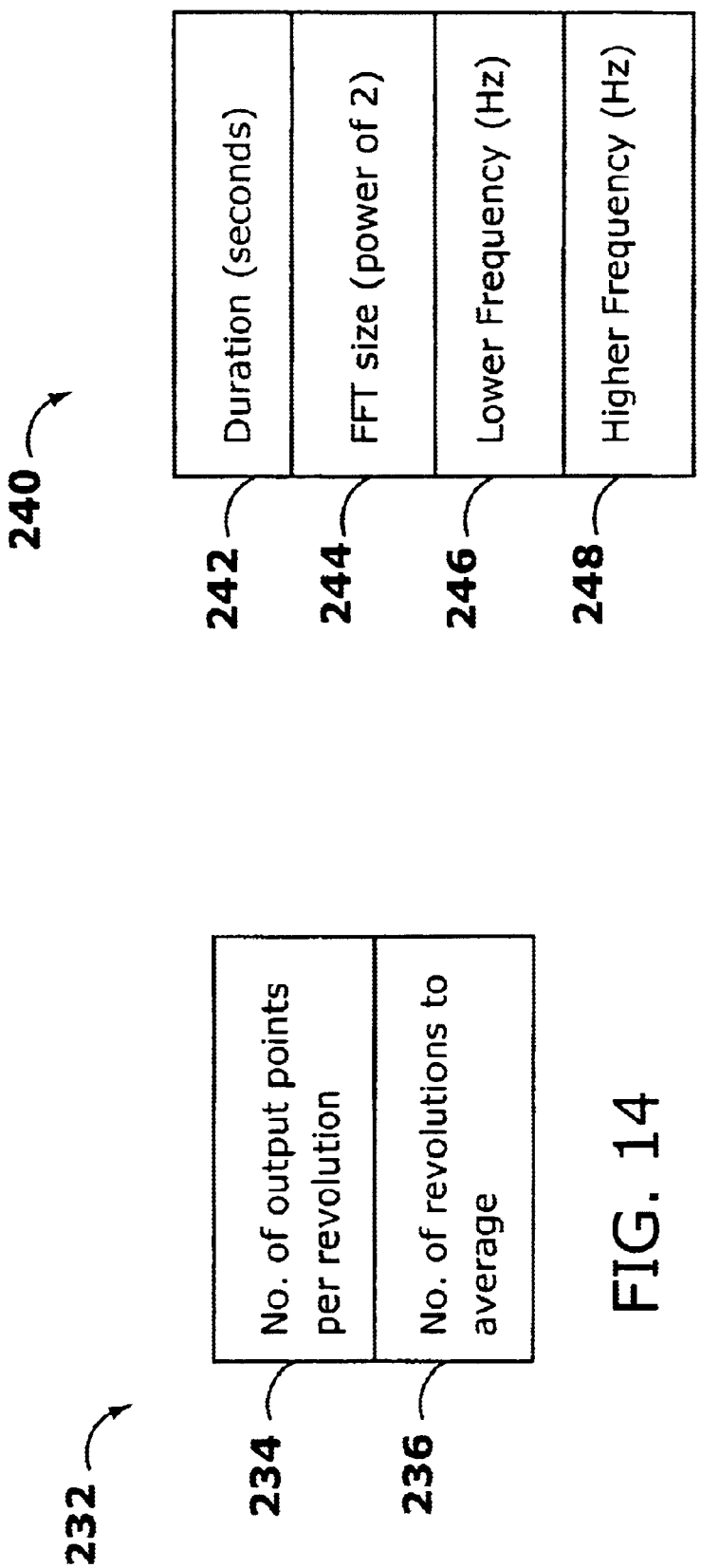

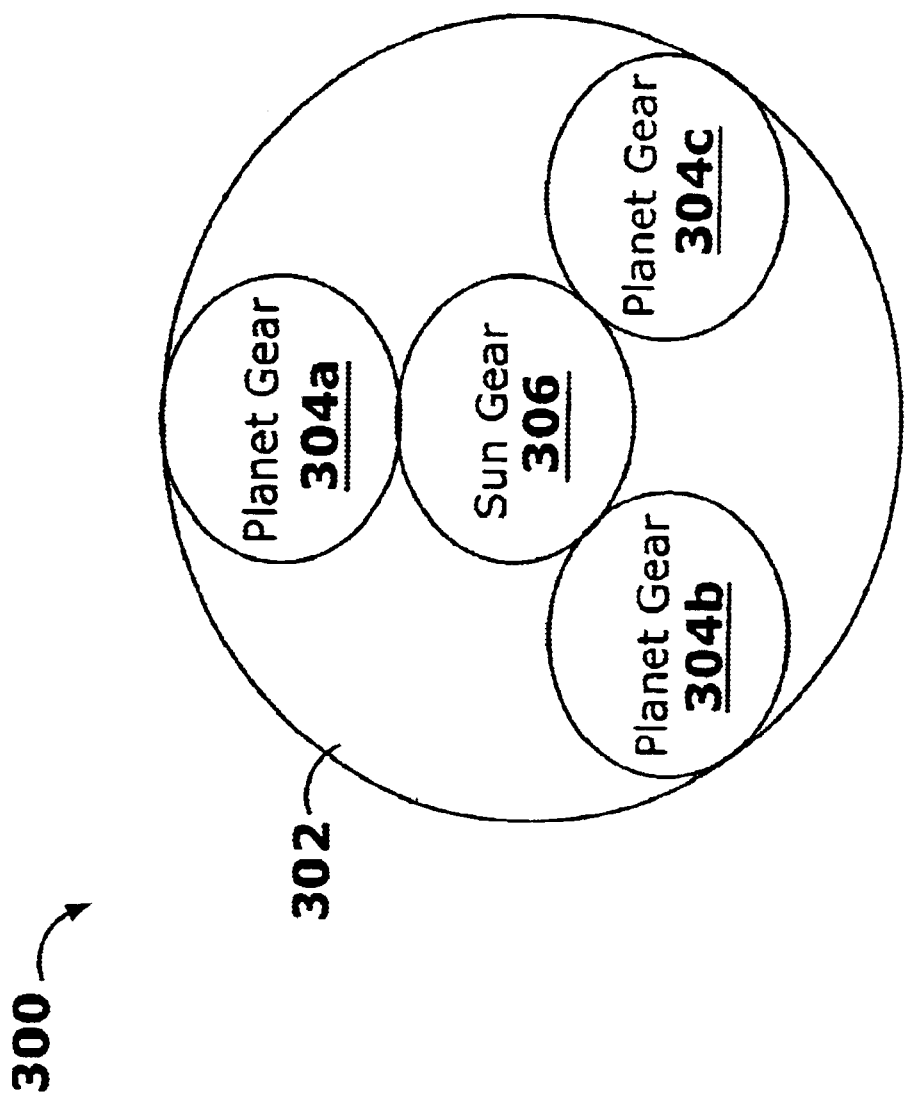

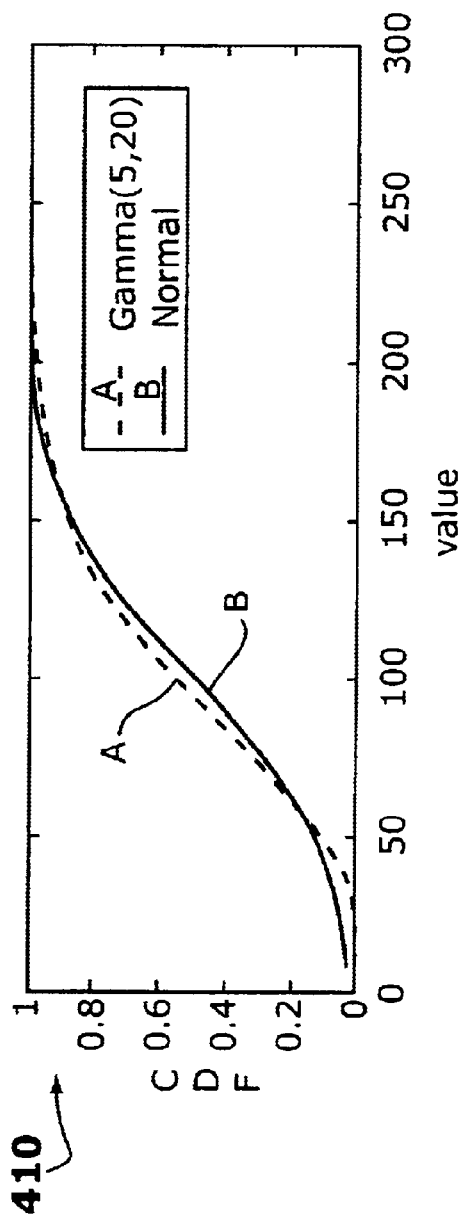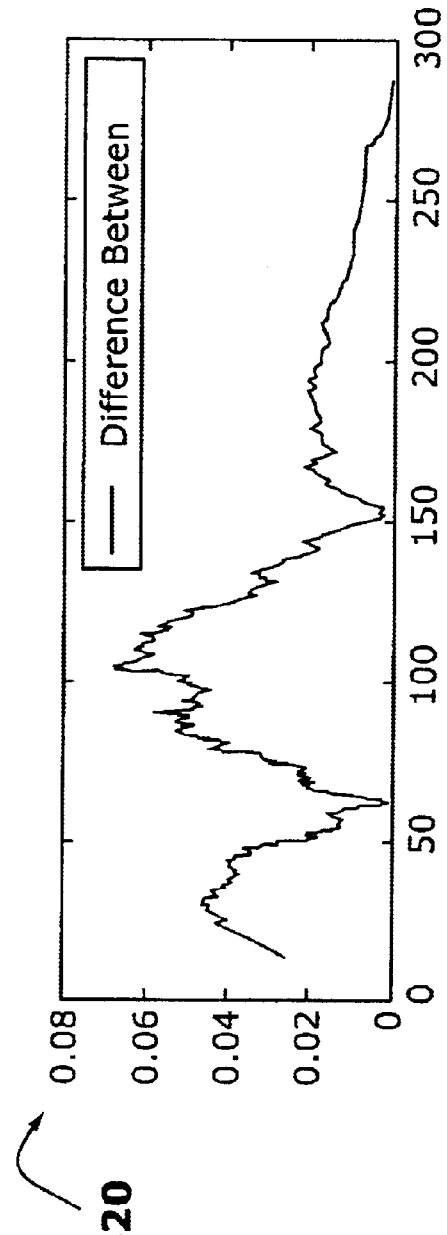
FIG. 20
FIG. 21

METHOD AND APPARATUS FOR DETERMINING THE HEALTH OF A COMPONENT USING CONDITION INDICATORS

CROSS REFERENCE TO RELATED APPLICATIONS

This application claims priority to U.S. Provisional patent application No. 60/293,331 filed on May 24, 2001 which is incorporated by reference herein.

BACKGROUND OF THE INVENTION

1. Field of the Invention

This application relates to the field of vibration analysis and more particularly to performing vibration analysis for the purpose of device monitoring.

2. Description of Related Art

The transmission of power to rotors which propel helicopters and other shafts that propel devices within the aircraft induce vibrations in the supporting structure. The vibrations occur at frequencies that correspond to the shaft rotation rate, mesh rate, bearing passing frequency, and harmonics thereof. The vibration is associated with transmission error (TE). Increased levels of TE are associated with transmission failure. Similar types of vibrations are produced by transmissions in fixed installations as well.

Parts, such as those that may be included in a helicopter transmission, may be replaced in accordance with a predetermined maintenance and parts replacement schedule. These schedules provide for replacement of parts prior to failure. The replacement schedules may indicate replacement time intervals that are too aggressive resulting in needless replacement of working parts. This may result in incurring unnecessary costs as airplane parts are expensive. Additionally, new equipment may have installed faulty or defective parts that may fail prematurely.

Thus it may be desirable to provide for an efficient technique for detecting part and device degradation without unnecessarily replacing parts. It may be desirable that this technique also provide for problem determination and detection prior to failure.

SUMMARY OF THE INVENTION

In accordance with one aspect of the invention are a method executed in a computer system and a computer program product for determining a health indicator associated with a component. A plurality of health classifications are determined. At least one condition indicator is determined quantifying a characteristic of the component. A probability associated with each of the health classifications is determined. The probability is an estimation that the component is of a particular health classification given the at least one indicator. A determination is made as to which of said health classifications is associated with said component using said probabilities associated with said health classifications for a given set of observed values.

In accordance with another aspect of the invention are a method executed in a computer system and a computer program product for determining a health status of a component. A plurality of condition indicators are selected having a value and each having a corresponding weighing factor, and at least one threshold value defining at least two classifications. A contribution to a health indicator is determined for each of the condition indicators, wherein the determining further comprises, for each of the plurality of indicators: determining which of the at least two classifications the value of each indicator belongs; and determining the contribution to the health indicator by each condition indicator in accordance with a selected one of the at least two classifications and the weighted value. The health indicator is determined in accordance with all contributions by each of the condition indicator values.

BRIEF DESCRIPTION OF DRAWINGS

Features and advantages of the present invention will become more apparent from the following detailed description of exemplary embodiments thereof taken in conjunction with the accompanying drawings in which:

FIG. 2 is an example representation of a data structure that includes aircraft mechanical data;

FIG. 3 is an example of parameters that may be included in the type-specific data portions when the descriptor type is an indexer;

FIG. 4 is an example of parameters that may be included in the type-specific data portions when the descriptor type is an accelerometer;

FIG. 5 is an example of parameters that may be included in the type-specific data portions when the descriptor type is a shaft;

FIG. 10 is a more detailed example of an embodiment of a header descriptor of FIG. 9;

FIG. 11 is an example of a descriptor that may be included in the acquisition descriptor group of FIG. 9;

FIG. 14 is an example of a descriptor that may be included in the signal average descriptor group of FIG. 9;

FIG. 15 is an example of a descriptor that may be included in the envelope descriptor group of FIG. 9;

FIG. 16 is an example of a planetary gear arrangement;

FIG. 20 is an example of a graphical representation of a cumulative distribution function (CDF) observed data following a gamma (5,20) distribution and the normal CDF;

FIG. 21 is an example of a graphical representation of the difference between the two CDFs of FIG. 20;

DETAILED DESCRIPTION OF THE PREFERRED EMBODIMENT(S)

Figure 1:
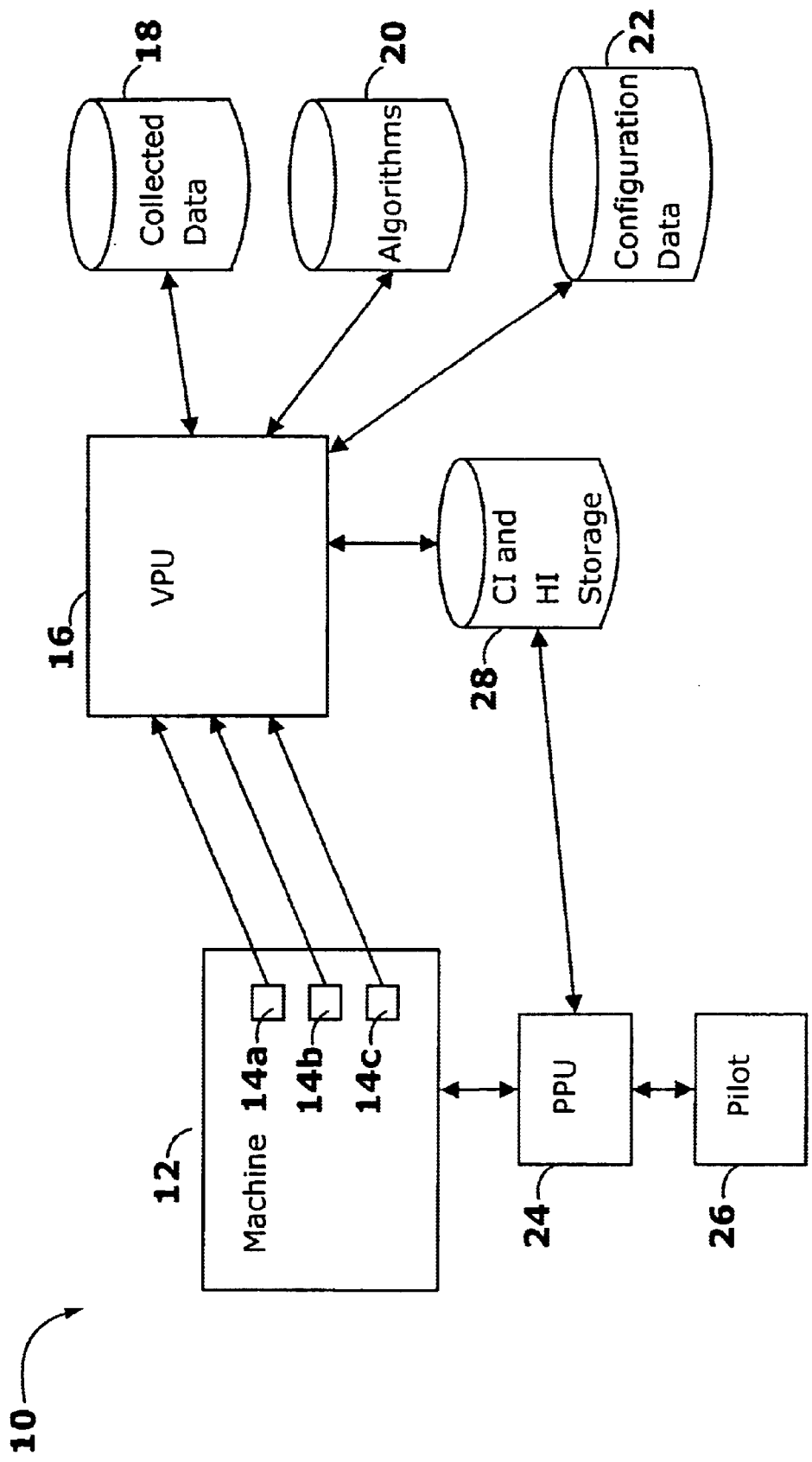
FIG. 1 is an example of an embodiment of a system that may be used in performing vibration analysis and performing associated monitoring functions.

Referring now to FIG. 1, shown is an example of an embodiment of a system 10 that may be used in performing vibration analysis and monitoring of a machine such as a portion of an aircraft. The machine being monitored 12 may be a particular element within an aircraft. Sensors 14a through 14c are located on the machine to gather data from one or more components of the machine. Data may be collected by the sensors 14a through 14c and sent to a processor or a VPU16 for data gathering and analysis. The VPU16 analyzes and gathers the data from the Sensors 14a through 14c.

The VPU16 may also use other data in performing analysis. For example, the VPU16 may use collected data 18. One or more of the Algorithms 20 may be used as input into the VPU16 in connection with analyzing data such as may be gathered from the Sensors 14a through 14c. Additionally, configuration data 22 may be used by the VPU16 in connection with performing an analysis of the data received for example from the Sensors 14a through 14c. Generally, configuration data may include parameters and the like that may be stored in a configuration data file. Each of these will be described in more detail in paragraphs that follow.

The VPU16 may use as input the collected data 18, one or more of the algorithms 20, and configuration data 22 to determine one or more condition indicators or CIs. In turn, these condition indicators may be used in determining health indicators or HIs that may be stored for example in CI and HI storage 28. CIs describe aspects about a particular component that may be useful in making a determination about the state or health of a component as may be reflected in an HI depending on one or more CIs. Generally, as will be described in more detail in paragraphs that follow, CIs and HIs may be used in connection with different techniques in determining an indication about monitored components such as Machine 12. As described in more detail elsewhere herein, the configuration data may include values for parameters that may vary in accordance with the type of the component being monitored.

It should be noted that the collected data 18 may include data collected over a period of time from sensors such as 14a through 14c mounted on Machine 12. A user, such as a Pilot 26, may use a special service processor, such as the PPU24, connected to the Machine 12 to obtain different types of data such as the CI and HI values 28.

As described in connection with FIG. 1, the VPU16 may receive inputs from Sensors 14a through 14c. These sensors may be different types of data gathering monitoring equipment including, for example, high resolution accelerometers and index sensors (indexors) or tachometers that may be mounted on a component of Machine 12 at carefully selected locations throughout an aircraft. Data from these sensors may be sampled at high rates, for example, up to 100 kilohertz, in order for the VPU16 to produce the necessary CI and HI indicators. Data from these sensors and accelerometers may be acquired synchronously at precise intervals in measuring vibration and rotational speeds.

Generally, the different types of data gathering equipment such as 14a–14c may be sensors or tachometers and accelerometers. Accelerometers may provide instantaneous acceleration data along whatever axis on which they are mounted of a particular device. Accelerometers may be used in gathering vibration analysis data and accordingly may be positioned to optimally monitor vibration generated by one or more mechanical components such as gears, shafts, bearings or planetary systems. Each component being monitored may generally be monitored using two independent sensors to provide confirmation of component faults and to enable detection of sensor faults.

No accelerometer is completely isolated from any other component. Thus, the component rotational frequencies share as few common divisors as possible in order to maximize the effectiveness of the monitoring function being performed. For example, all gears being monitored should have differing number of teeth and all bearings should have differing numbers and sizes of balls or rollers. This may allow individual components to be spectrally isolated from each other to the extent that their rotational frequencies are unique.

The indexers (index sensors) or tachometers may also be used as a particular monitoring component 14a through 14c to gather data about a particular component of Machine 12. The indexers produce a periodic analog signal whose frequency is an integer multiple of the instantaneous rotation frequency of the shaft that they are monitoring. These signals may be generated magnetically using one or more evenly spaced metallic protrusions on the shaft passing by the fixed sensor. Alternatively, these may be monitored optically using a piece of optically reflective material affixed to the shaft. It should be noted that each index point should be fixed in time as precisely as possible. In connection with magnetic sensors, this may be accomplished for example by interpolating the zero crossing times of each index pulse and similarly for optical sensors by locating either rising or falling edges. Assuming the minimal play or strain in the drive train when something is under load, the relative position and rate of any component may be calculated using a single index or wave form.

Because of the high data rates and lengthy processing intervals, diagnostics may be performed, for example, on pilot command or on a predetermined flight regime or time interval.

Each of the algorithms 20 produces one or more CIs described elsewhere herein in more detail. Generally, the CI may yield useful information about the health of a monitored component. This condition indicator or CI as well as HI may be used in determining or predicting faults of different components.

It should be noted that the VPU16 is intended to be used in a wide variety of mechanical and electrical environments. As described herein, different components of an aircraft may be monitored. However, this is only one example of a type of environment in which the system described herein may be used. As known to those skilled in the art, the general principles and techniques described herein have much broader and general applicability beyond a specific aircraft environment that may used in an example here.

In connection with the use of CIs, the VPU16 uses the CIs as input and portions of the data such as, for example, used in connection with an algorithm to provide HIs. These are described in more detail in paragraphs that follow.

It should be noted that in a particular embodiment, each mechanical part being monitored may have one or more sensors associated with it where a sensor may include for example an accelerometer or a tachometer. Generally, accelerometers may be used, for example, to obtain data regarding vibrations and a tachometer may be used, for example, to gain information and data regarding rotation or speed of a particular object. Data may be obtained and converted from the time to the frequency domain.

A particular algorithm may provide one or more CIs. Each of the algorithms may produce or be associated with a particular CI. One or more CIs may be used in combination with a function to produce an HI for a particular part or type. As will be described in more detail herein, each of the algorithms may be associated or classified with a particular part or type. The CI generally measures vibrations and applies a function as described in accordance for each algorithm. Generally, vibration is a function of the rotational frequency in the amount of torque. Using torque and a particular frequency, a CI is appropriately determined in accordance with a selected algorithm for a part.

The algorithms 20 may be classified into four families or groups in accordance with the different types of parts. In this example, the families of algorithms may include shaft, gears, bearings, and planetary gears. Associated with each particular part being monitored may be a number of CIs. Each CI may be the result or output of applying a different one of the algorithms for a particular family. For example, in one embodiment, each gear may have an associated 27 CIs, each bearing may have 19 CIs, each shaft may have 22 CIs, and each planetary gear may have two or three CIs. It should be noted that each one of these numbers represents in this example a maximum number of CIs that may be used or associated with a particular type in accordance with the number of algorithms associated with a particular class or family. Generally, the different number of CIs that may be associated with a particular type such as a gear try to take into account the many different ways in which a particular gear may fail. Thus, a CI reflects a particular aspect or characteristic about a gear with regard to how it may fail. Different techniques used in computing CIs are described, for example, in "Introduction to Machinery Analysis and Monitoring, Second Edition", 1993, Penn Well Publishing Company of Tulsa, Okla., ISBN 0-87814-401-3, and "Machinery Vibration: measurement and analysis", 1991, McGraw-Hill Publishing, ISBN-0-07-071936-5.

Referring now to FIG. 2, shown is an example of a data structure 50 that includes aircraft mechanical data. Generally, this data structure includes one or more descriptors 56a through 56n. In this embodiment there may be one descriptor for each sensor. A descriptor associated with a particular sensor includes the parameters relevant to the particular component being monitored. Each of the descriptors such as 56a includes three portions of data. The field 52 identifies a particular type of descriptor. Each of the descriptors also includes a common data portion 54 which includes those data fields common to all descriptor types. Also included is a type specific data portion 56 which includes different data fields, for example, that may vary in accordance with the descriptor type 52.

Descriptor types may include, for example, an indexer, an accelerometer, a shaft, a gear, a planetary gear, or a bearing descriptor type value corresponding to each of the different types of descriptors. The common data portion 54 may include, for example, a name, part number and identifier. In this example, the identifier in the common data filed 54 may uniquely identify the component and type.

Referring now to FIGS. 3 through 8, what will be described are examples of descriptor type specific parameters or information that may be included in a descriptor of a particular type, such as in area 56 of the data structure 50.

Referring now to FIG. 3, shown is an example of parameters that may be included in a descriptor 60 which is an indexer descriptor type. The parameters that may be included are a channel 62, a type 64, a shaft identifier 66, a pulses per revolution parameter 68, a pulse width parameter 70, and a frequency of interest 72 for this particular type of descriptor. It should be noted that the type in this example for the index or descriptor may be one of sinusoidal, pulse such as 1/rev, or optical. The shaft identifier 66 is that as may be read or viewed by the indexer that calculates the shaft rate. The pulse width 70 is in seconds as the unit value. Additionally, the frequency of interest 72 for this descriptor type is a nominal pulse frequency that is used in computing the data quality signal to noise ratio. The use of these particular data structures and parameters is described in more detail in paragraphs that follow.

Referring now to FIG. 4, shown is an example of the parameters that may be included in an accelerometer descriptor type 80. The descriptor for an accelerometer type may include the channel 82, a type 84, a sensitivity 86 and a frequency of interest 88. In this example for the accelerometer descriptor type, the type may be one of normal, or remote charge coupled. The frequency of interest may be used in computing the data quality signal to noise ratio. The frequency of interest for a gear is the mesh rate which may be calculated from the gear shaft rate and the number of teeth of the gear.

Referring now to FIG. 5, shown is an example of descriptor type specific parameters or data that may be included when a descriptor type is the shaft descriptor. A shaft descriptor 90 includes path parameter or data 92 and nominal RPM data 94. The path data is an even length sequence of gear tooth counts in the mechanical path between the shaft in question and a reference shaft. The driving gears alternate with driven gears such that the expected frequency of a gear, shaft, bearing and the like may be determined based on an input shaft RPM.

Figures 6, 7:
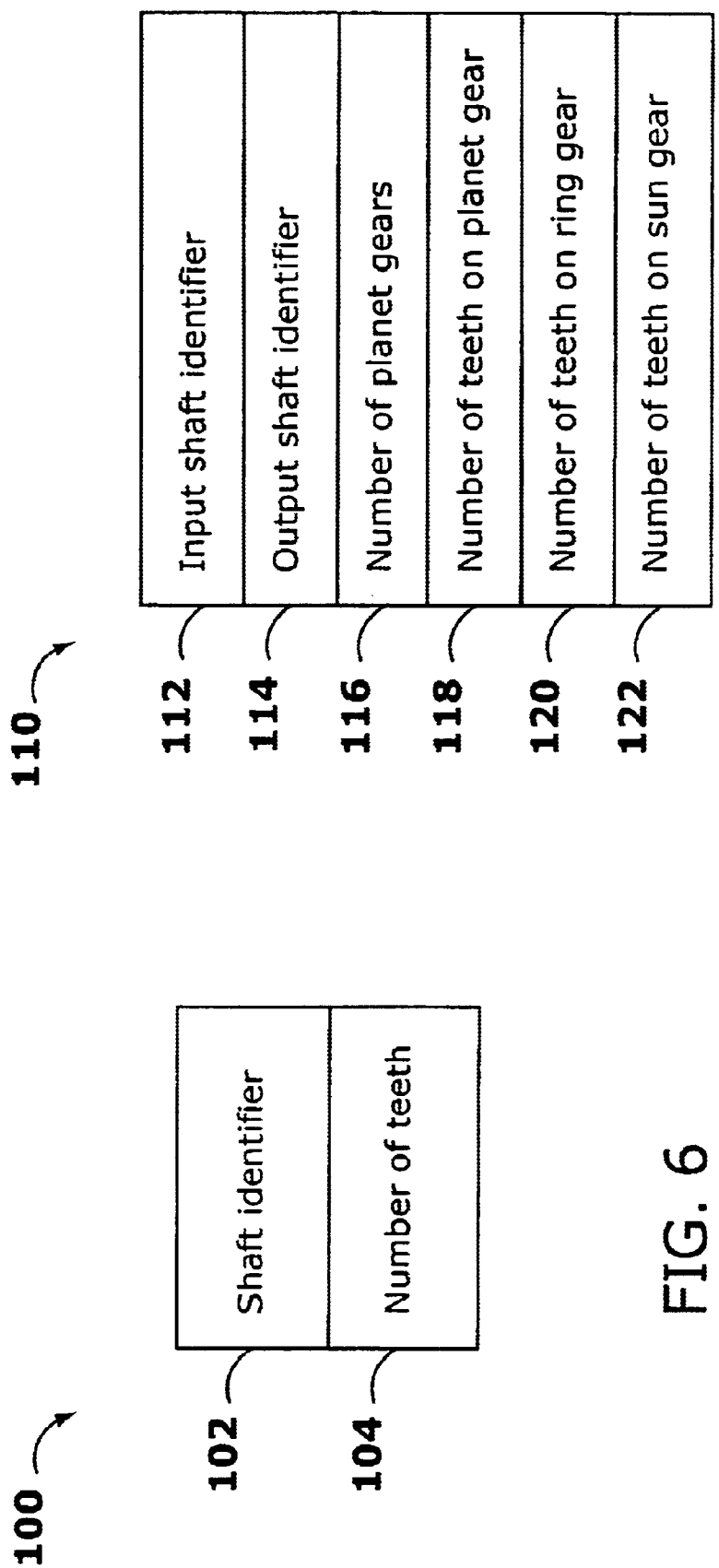
FIG. 6 is an example of parameters that may be included in the type-specific data portions when the descriptor type is for a gear.
FIG. 7 is an example of parameters that may be included in the type-specific data portions when the descriptor type is a planetary type.

Referring now to FIG. 6, shown is an example of data or parameters that may be included in a descriptor when the descriptor type is the gear descriptor. Included in the gear descriptor 100 is the shaft identifier 102 to which the gear is mounted and a parameter 104 indicating the number of teeth in the gear.

Referring now to FIG. 7, shown is an example of an embodiment of a planetary descriptor 110 identifying those parameters or data that may be included when the type is a planetary descriptor type. The planetary descriptor 110 may include an input shaft identifier 112, an output shaft identifier 114, a parameter indicating the number of planet gears 116, a parameter indicating the number of teeth on the planet gear, a parameter 120 indicating the number of teeth on the ring gear, and a parameter 122 indicating the number of teeth on the sun gear. It should be noted that the number of teeth on a planet gear relates to a planet carrier that is assumed to be mounted to the output shaft. Additionally, the ring gear is described by parameter 120 is assumed to be stationery and the sun gear 122 as related to parameter 122 is assumed to be mounted to the input shaft. It should be noted that the path between the input and the output shaft may be reduced to using a value S for the driving path tooth count and R+S as the driven path tooth count where R and S are the ring and sun tooth counts respectively. An example of a planetary type gear is described in more detail elsewhere herein.

Figure 8:
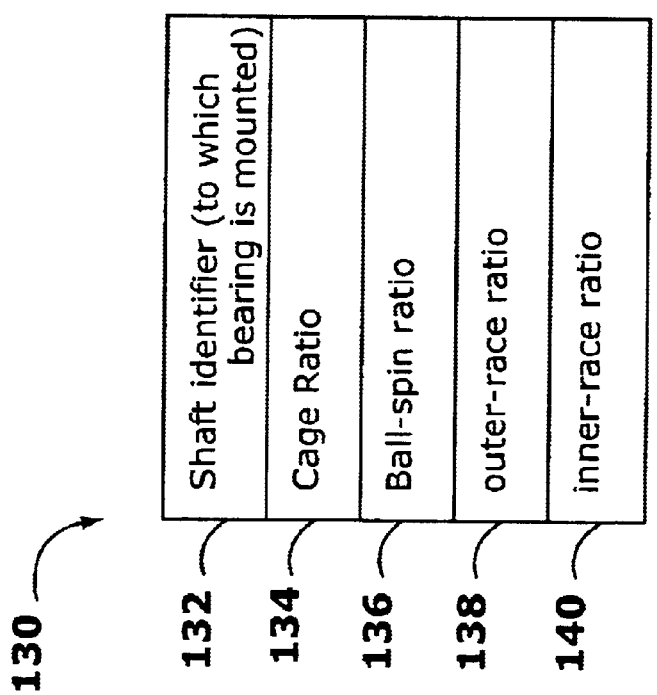
FIG. 8 is an example of parameters that may be included in the type-specific data portions when the descriptor type is bearing type.

Referring now to FIG. 8, shown is an example of a bearing descriptor 130. The bearing descriptor 130 may include descriptor type specific fields including a shaft identifier 132, a cage ratio 134, a ball spin ratio 136, an outer race ratio 138 and an inner race ratio 140. An example of a bearing is described in more detail elsewhere herein.

It should be noted that the data structures described in connection with FIGS. 2 through 8 are those that may be used in storing data obtained and gathered by a sensor such as 14a when monitoring a particular component of a machine 12. Data may be gathered and stored in the data structure for a particular descriptor or descriptors and sent to the VPU 16 for processing. It should be noted that a particular set of data may be gathered at a particular instance and time, for example, in connection with the synchronous data gathering described elsewhere herein. In connection with this, a data set may include multiple descriptors from sampling data at a particular point in time which is sent to the VPU 16.

What will now be described are those data structures that may be associated with an analysis definition that consists of a specific data acquisition and a subsequent processing of this data to produce a set of indicators for each of the desired components.

Figure 9:
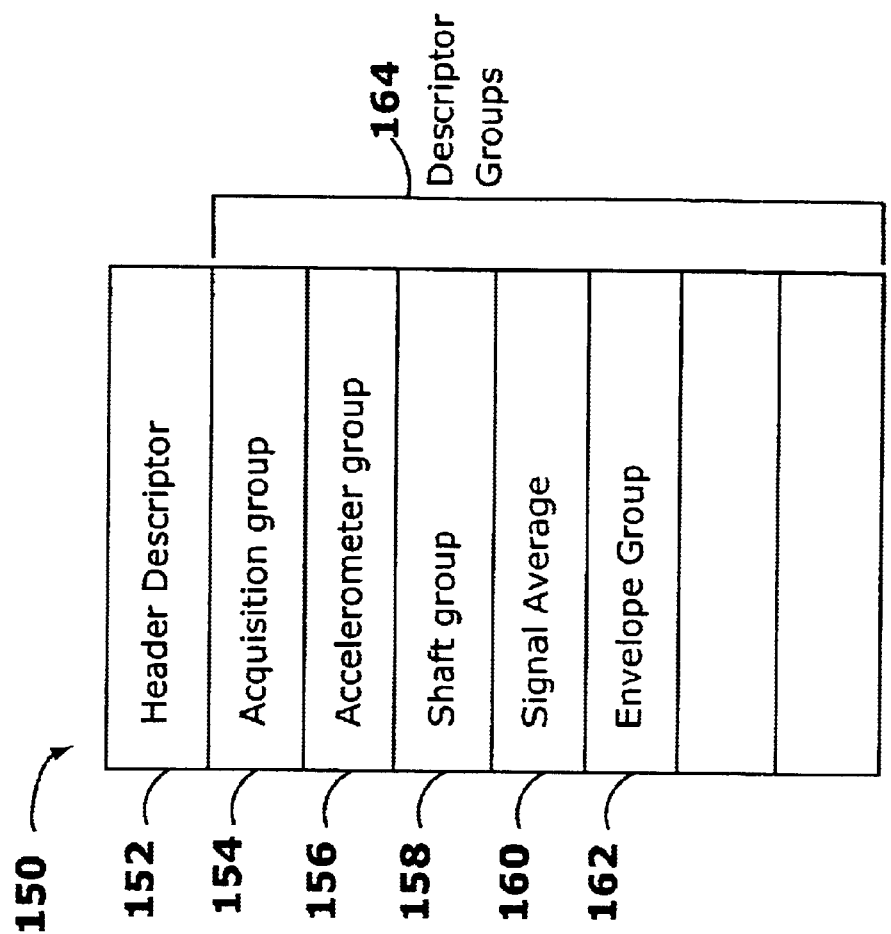
FIG. 9 is an example of a data structure that includes analysis information.

Referring now to FIG. 9, shown is an example of the data structure 150 that contains analysis data. Each instance of analysis data 150 as represented in the data structure includes a header descriptor 152 and descriptor groups noted as 164. In this example there are five descriptor groups although the particular number may vary in an embodiment. Each of the descriptor groups 154 through 162 as identified by the group identifier 164 includes one or more descriptors associated with a particular group type. For example, descriptor group 154 is the acquisition group that includes a descriptor for each sensor to be acquired. The accelerometer group 156 consists of a descriptor for each accelerometer to be processed. The shaft group 158 includes a descriptor for each shaft to be processed. The signal average group 160 includes a descriptor for each unique parameter set. The envelope group 162 includes a descriptor for each unique parameter.

Referring now to FIG. 10, shown is a more detailed example of a header descriptor 170. Parameters that may be included in a header descriptor 170 include: an analysis identifier 172, acquisition time out parameter 174 and processing time out parameter 176. In this example, the acquisition, time out and processing time out parameters are in seconds.

Referring now to FIG. 11, shown is an example of a descriptor that may be included in the acquisition group. A descriptor 180 included in the acquisition group may include a sensor identifier 182, a sample rate parameter in Hz 184, a sample duration in seconds 186, a gain control setting, such as "auto" or "fixed" 188, an automatic gain control (AGC) acquisition time in seconds 190, an automatic gain control (AGC) headroom factor as a number of bits 192 and a DC offset compensation enable 194.

Figure 12:
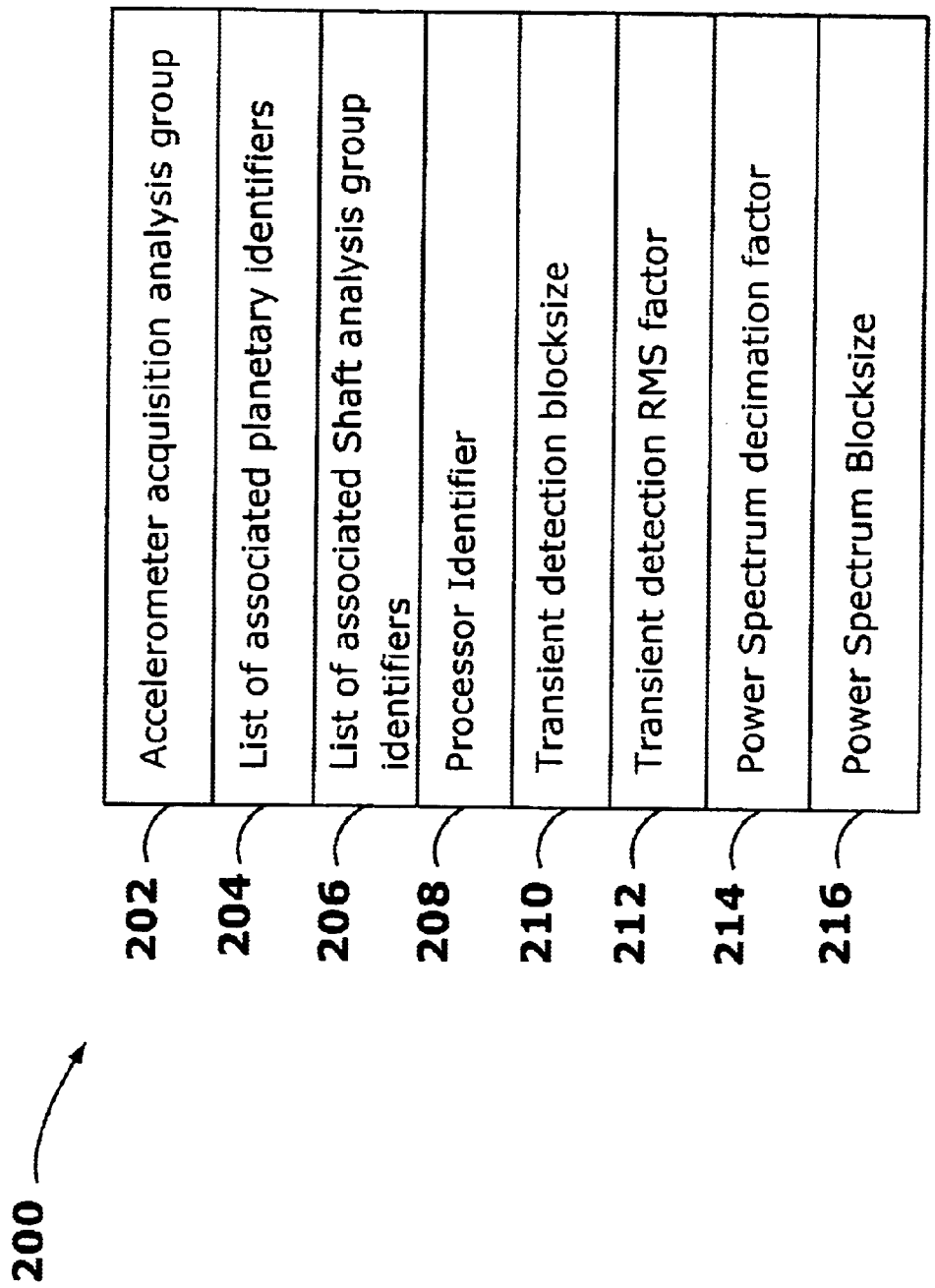
FIG. 12 is an example of a descriptor that may be included in the accelerometer group of FIG. 9.

Referring now to FIG. 12, shown is an example of a descriptor 200 that may be included in the accelerometer group. A descriptor in the accelerometer group may include a parameter that is an accelerometer acquisition analysis group identifier 202, a list of associated planetary identifiers to be processed 204, a list of associated shaft analysis group identifiers to be processed 206, a processor identifier 208, a transient detection block size 210, a transient detection RMS factor 212, a power spectrum decimation factor 214 specified as a power of 2 and a power spectrum block size also specified as a power of 2.

In one embodiment, the list of associated planetary identifiers 204 also includes two signal average analysis group identifiers for each planetary identifier, first identifier corresponding to the input shaft and a second corresponding to an output shaft.

It should be noted that the processor identifier 208 will be used in connection with assigning processing to a particular DSP or digital signal processor.

Figure 13:
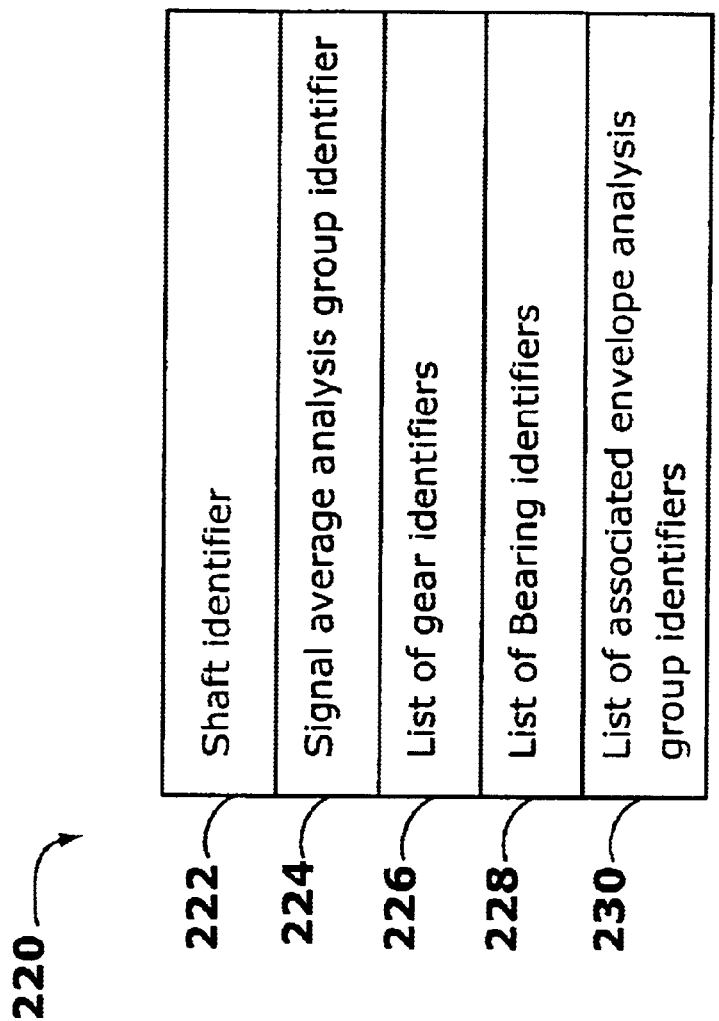
FIG. 13 is an example of a descriptor that may be included in the shaft descriptor group of FIG. 9.

Referring now to FIG. 13, shown is an example of an embodiment of a descriptor 280 that may be included in the shaft group. The descriptor 220 may include a shaft identifier 222, a signal average analysis group identifier 224, a list of gear identifiers to be processed 226, a list of bearing identifiers to be processed 228 and a list of associated envelope analysis group identifiers 230.

Referring now to FIG. 14, shown is an example of a descriptor 232 that may be included in the signal average group. It should be noted that the signal average group includes a descriptor for each unique parameter set. The signal average processing group is run for each accelerometer and shaft combination even if it has the same parameters as another combination. Each descriptor 232 may include a number of output points per revolution 234 and a number of revolutions to average 236.

Referring now to FIG. 15, shown is an example of a descriptor 240 that may included in the envelope group. It should be noted that the envelope group includes a descriptor for each unique parameter. It is not necessary to repeat an envelope processing for each bearing if the parameters are the same. Each descriptor 240 may include a duration parameter 242 specifying the seconds of raw data to process, an FFT size 244 which is a power of 2, a lower bound frequency in Hz 246, and an upper bound frequency, also in, Hz 248.

Referring now to FIG. 16, shown is an example of an embodiment 300 of a planetary gear arrangement. Generally, a planetary gear arrangement as described in connection with the different types of gears and items to be monitored by the system 10 of FIG. 1 may include a plurality of gears as configured, for example, in the embodiment 300. Included in the arrangement 300 is a ring gear 302 a plurality of planet gears 304*a* through 304*c* and of sun gear 306. Generally, the gears that are designated as planets move around the sun gear similar to that as a solar system, hence the name of planet gear versus sun gear. The arrangement shown in FIG. 16 is a downward view representing the different types of gears included in an arrangement 300.

Figures 17A, 17B:
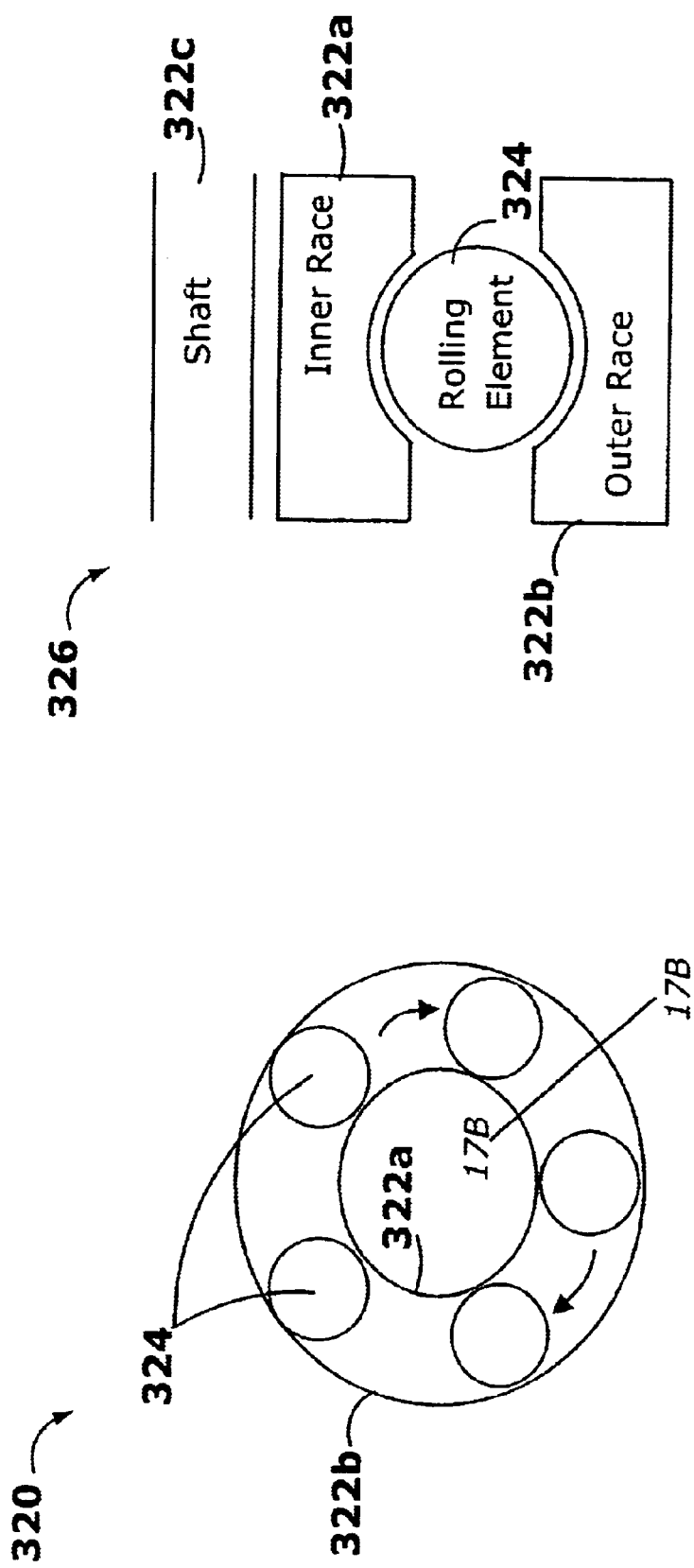
FIG. 17A is an example of an embodiment of a bearing.
FIG. 17B is an example of a cut along a line of FIG. 17A.

Referring now to FIG. 17A, shown is an example of an embodiment 320 of a bearing. The bearing 320 includes a ring or track having one or more spherical or cylindrical elements (rolling elements) 324 moving in the direction of circular rotation as indicated by the arrows. Different characteristics about such a structure of a bearing may be important as described in connection with this embodiment. One characteristic is an "inner race" which represents the circumference of circle 322*a* of the inner portion of the ring. Similarly, the "outer race" or circumference 322*b* representing the outer portion of the ring may be a consideration in connection with a bearing.

Referring now to FIG. 17B, shown is an example of a cut along line 17B of FIG. 17A. Generally, this is cut through the ring or track within which a bearing or bearings 324 rotate in a circular direction. The ball bearings move in unison with respect to the shaft within a cage that follows a track as well as rotate around each of their own axis.

Figure 18A:
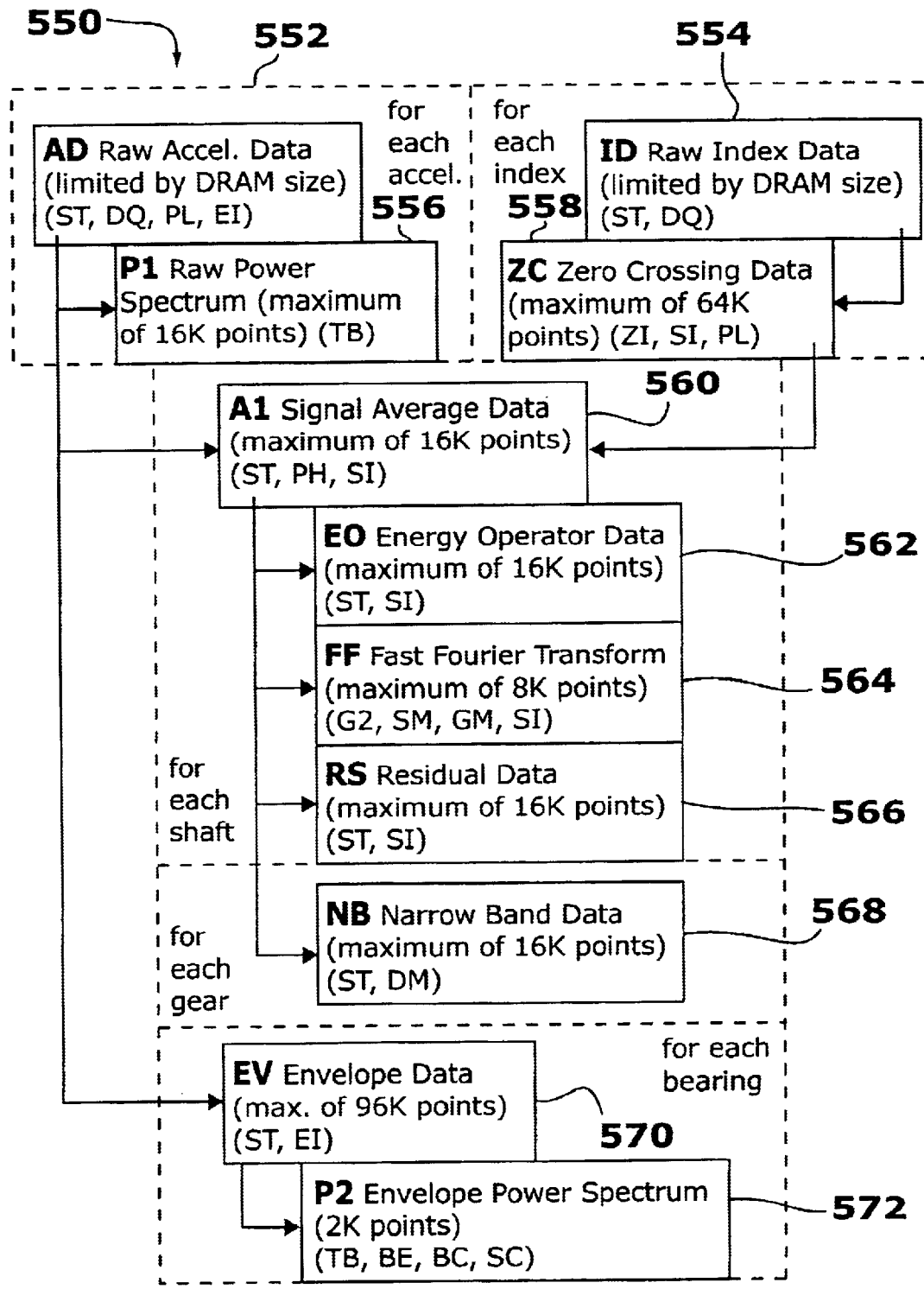
FIG. 18A is an example of a representation of data flow in vector transformations.

Referring now to FIG. 18A, shown is an example of a representation 550 of different transformations that may be performed and the associated data flow and dependencies for each particular sensor. The output of the transformations are transformation vectors and may be used in addition to analysis data or raw data, such as bearing frequency, mesh frequency, and the like, by an algorithm in producing a CI.

Referring to the representation 550, an in going arrow represents data flow input to a transformation. For example, the FF or Fast Fourier transform takes as an input data from the A1 signal average data transform. A1 has as input the accelerometer data AD. It should be noted that other embodiments may produce different vectors and organize data inputs/outputs and intermediate calculations in a variety of different ways as known to those skilled in the art.

Figure 18B:
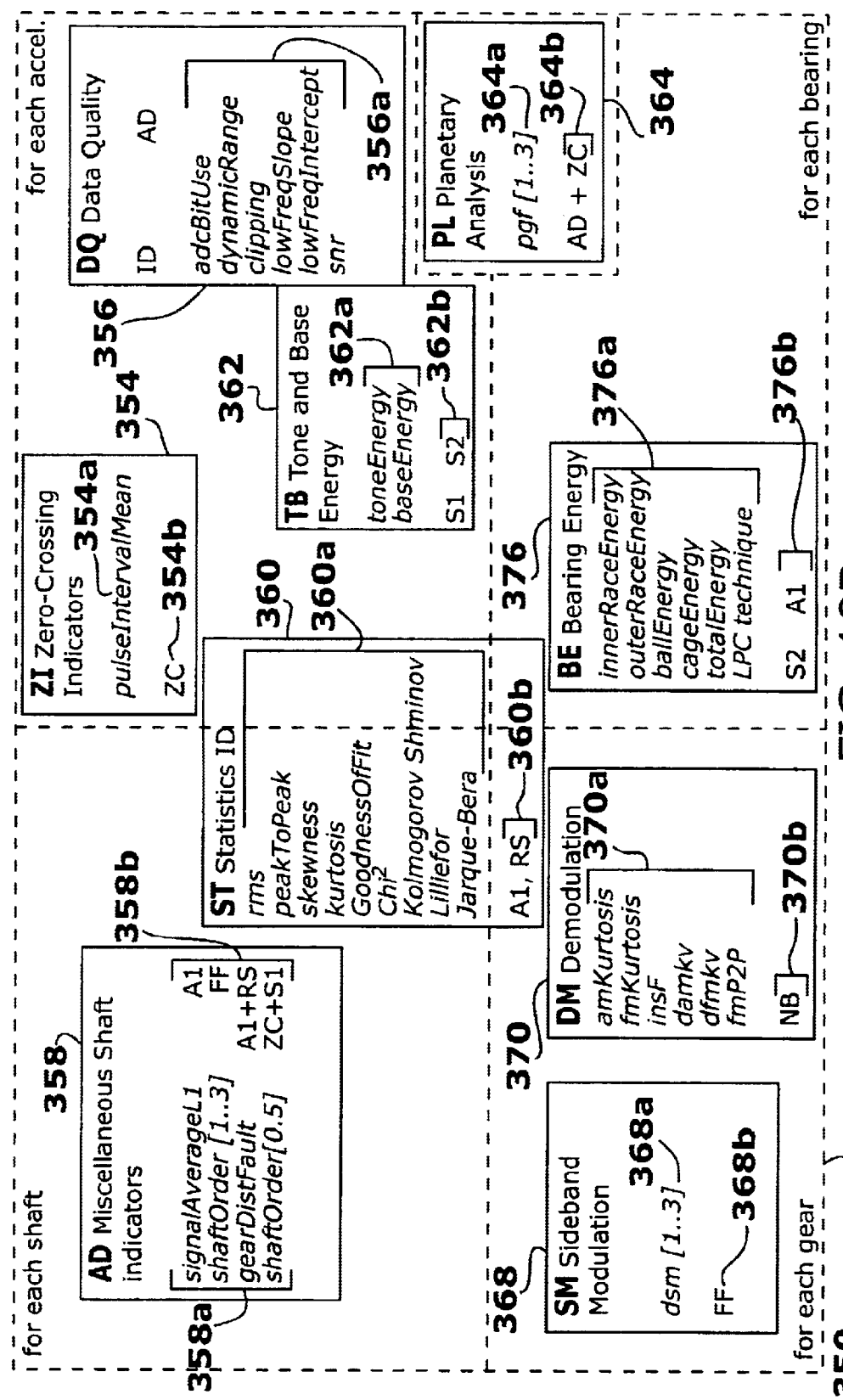
FIG. 18B is an example of a representation of some of the CI algorithms that may be included in an embodiment, and some of the various inputs and outputs of each.

Referring now to FIG. 18B, shown is an example of a representation 350 relating algorithms, a portion of input data, such as some transformation vectors, and CIs produced for each type of component, that may be included in an embodiment. Other embodiments may use different data entities in addition to those shown in connection with FIG. 18B. As described elsewhere herein, each type of component in this example is one of: indexer, accelerometer, shaft, gear, planetary, or bearing. Certain algorithms may be used in connection with determining one or more CIs for more than one component type. It should be noted that a variety of different algorithms may be used and are known by one of ordinary skill in the art, as described elsewhere herein in more detail. The following are examples of some of the different techniques that may be used in producing CIs. Additionally, FIG. 18B illustrates an example of relationships between some algorithms, a portion of their respective inputs and outputs, as well as how the algorithms may be associated with different component types. However, it should be noted that this illustration is not all inclusive of all algorithms, all respective inputs and outputs, and all component types.

What will now be described are algorithms and the one or more CIs produced that may be included in an embodiment. It should be noted that the number and type of algorithms included may vary in accordance with an embodiment. Additionally, it should be noted that FIG. 18B may not include each and every input and output for an algorithm as described herein and other embodiments of the algorithms described generally herein may also vary.

The data quality (DQ) algorithm 356 may be used as a quality assurance tool for the DTD CI. DQ performs an assessment of the raw uncalibrated sensor data to insure that the entire system is performing nominally. DQ may be used to identify, for example, bad wiring connections, faulty sensors, clipping, and other typical data acquisition problems. The DQ indicator checks the output of an accelerometer for "bad data". Such "bad data" causes the SI to be also be "bad" and should not be used in determining health calculations.

What will now be described are the different indicators that may be included in an embodiment of the DQ algorithm. ADC Bit Use measures the number of ADC bits used in the current acquisition. The ADC board is typically a 16 bit processor. The log base 2 value of the maximum raw data bit acquired is rounded up to the next highest integer. Channels with inadequate dynamic range typically use less than 6 bits to represent the entire dynamic range. ADC Sensor Range is the maximum range of the raw acquired data. This range cannot exceed the operational range of the ADC board, and the threshold value of 32500 is just below the maximum permissible value of +32767 or −32768 when the absolute value is taken. Dynamic Range is similar to the ADC Sensor Range, except the indicator reports dynamic channel range as a percent rather than a fixed bit number. Clipping indicates the number of observations of clipping in the raw data. For a specific gain value, the raw ADC bit values cannot exceed a specific calculated value. Low Frequency Slope (LowFreqSlope) and Low Frequency Intercept (lowFreqInt) use the first 10 points of the power spectral density calculated from the raw data and perform a simple linear regression to obtain the intercept and slope in the frequency-amplitude domain. SNR is the signal to noise ratio observed in each specific data channel. A power spectral density is calculated from the raw uncalibrated vibration data. For each data channel, there are known frequencies associated with certain components. Examples include, but are not limited to, gear mesh frequencies, shaft rotation rates, and indexer pulse rates. SNR measures the rise of a known tone (corrected for operational speed differences) above the typical minimum baseline levels in a user-defined bandwidth (generally +/−8 bins).

The Statistics (ST) algorithm 360 is associated with producing a plurality of statistical indicators 360*a*. The Root-Mean-Square (RMS) value of the raw vibration amplitude represents the overall energy level of the vibration. The RMS value can be used to detect major overall changes in the vibration level. The Peak-To-Peak value of the raw vibrating amplitude represents the difference between the two vibration extrema. When failures occur, the vibration amplitude tends to increase in both upward and downward directions and thus the Peak-To-Peak value increases. The Skewness coefficient (which is the third statistical moment) measures the asymmetry of the probability density function (p.d.f.) of the raw vibration amplitude. Since it is generally believed that the p.d.f. is near Gaussian and has a Skewness coefficient of zero, any large deviations of this value from zero may be an indication of faults. A localized defect in a machine usually results in impulsive peaks in the raw vibration signal, which affects the tails of the p.d.f. of the vibration amplitude. The fourth moment (Kurtosis) of the distribution has the ability to enhance the sensitivity of such tail changes. It has a value of 3 (Gaussian distribution) when the machinery is healthy. Kurtosis values larger than 3.5 are usually an indication of localized defects. However, distributed defects such as wear tend to smooth the distribution and thus decrease the Kurtosis values.

The ST algorithm may be performed on the following vectors: AD raw accelerometer data, A1 signal average data, RS residual data, NB narrow band data, and EV envelope data and others, some of which are listed in 360b.

The Tone andbase Energy algorithm(TB) 362 uses tone energy and base energy. Tone Energy is calculated as the sum of all the strong tones in the raw vibration spectrum. Localized defects tend to increase the energy levels of the strong tones. This indicator is designed to provide an overall indication of localized defects. "Strong tones" are determined by applying a threshold which is set based on the mean of all the energy contents in the spectrum. Any tones that are above this threshold are attributed to this indicator. The Base Energy measures the remaining energy level when all the strong tones are removed from the raw vibration spectrum. Certain failures such as wear, do not seem to affect the strong tones created by shaft rotation and gear mesh, the energy in the base of the spectrum could potentially be a powerful detection indicator for wear-related failures. Note that the sum of Tone Energy and Base Energy equals the overall energy level in the spectrum.

SI are miscellaneous shaft indicators. SO1 (Shaft Order 1 in g) is the once-per-rev energy in the signal average, and is used to detect shaft imbalance. SO2 (Shaft Order 2 in g) is the twice-per-rev energy in the signal average, and is used to detect shaft misalignment. GDF (Gear detector fault) may be an effective detector for distributed gear faults such as wear and multiple tooth cracks, and is a complement of the indicator signalAverageL1 (also known as gearLocalFault).

In addition to the specifically referenced vectors below, the SI algorithm takes input from the indexer zero-crossing vector (ZC).

The Demodulation analysis (DM) 370 is designed to further reveal side band modulation by using the Hilbert transform on either the narrow band signal (narrow band demodulation) or the signal average itself (wide band demodulation) to produce the Amplitude Modulation (AM) and Phase Modulation (FM) signals. The procedures involved to obtain such signals are:

Perform Hilbert transform on the narrow band signal (or signal average).
Compute the amplitude of the obtained complex analytic signal to obtain the AM signal.
Compute the phase angles of the analytic signal to obtain the FM signal.
Compute the instantaneous amplitude of the analytic signal to obtain the dAM signal.
Compute the instantaneous phase angles of the analytic signal to obtain the dFM signal.

The DM algorithm is performed on the band passed filtered data at a frequency of interest by taking a Hilbert Window function of the frequency domain data and converting the data back to the time domain.

The Sideband Modulation (SM) 368 analysis is designed to reveal any sideband activities that may be the results of certain gear faults such as eccentricity, misalignment, or looseness. CIs included in 368a are DSMn. DSMn is an indicator that characterizes the Degree of Sideband Modulation for the nth sideband (n=1, 2, and 3). The DSMn is calculated as the sum of both the nth high and low sideband energies around the strongest gear meshing harmonic. As indicated in 368b, the SM algorithm is performed on the Fast Fourier transform vector (FF).

The Planetary Analysis (PL) 364 extracts the Amplitude Modulation (AM) signal produced by individual planet gears and compares the "uniformity" of all the modulation signals. In general, when each planet gear orbits between the sun and the ring gears, its vibration modulates the vibration generated by the two gears. It is believed that when one of the planet gears is faulty, the amplitude modulation of that planet gear would behave differently than the rest of the planet gears. The procedure to perform this algorithm is to obtain signal averages for the input, output, and planet shafts. For each signal average:

Locate the strongest gear meshing harmonic.
Bandpass filter the signal average around this frequency, with the bandwidth equals to twice the number of planet gears.
Hilbert transform the bandpass filtered signal to obtain the AM signal.
Find the maximum(MAX) and minimum(MIN) of the AM signal.
Calculate the Planet Gear Fault (PGF) indicator as included in 364a according to the equation PGF= MAX(AM)/MIN (AM).

The inputs to the PL algorithm are the raw accelerometer data (AD) and the indexer zero-crossing data (ZC).

The Zero-Crossing Indicators (ZI) algorithm 354 is performed on the zero-crossing vector (ZC). The zero crossing indicators may be determined as follows:

$D_j = In_{j+1} - In_j$, j=0 . . . N−2, the stored zero-crossing intervals pulseIntervalMean=Mean($D$)

The Shaft Indicators (SI) algorithm 358 calculates miscellaneous shaft indicators included in 358a. SO1 (Shaft Order 1 in g) is the once-per-rev energy in the signal average, and is used to detect shaft imbalance. SO2 (Shaft Order 2 in g) is the twice-per-rev energy in the signal average, and is used to detect shaft misalignment.

SO3 (Shaft Order 3), is the three-per-rev energy in the signal average, and is used to detect shaft misalignment. The miscellaneous shaft indicators may also be included in an embodiment defined as follows:

$p = numPathPairs$ $$shaftRatio = \frac{\prod_{i=0}^{p-1} shaftPath_{2i}}{\prod_{i=0}^{p-1} shaftPath_{2i+1}} = \frac{driving}{driven}$$

$$indexRatio = \frac{\prod_{i=0}^{p-1} indexPath_{2i}}{\prod_{i=0}^{p-1} indexPath_{2i+1}} = \frac{driving}{driven}$$

$$driveRatio = \frac{indexRatio}{shaftRatio} \cdot pulsesUsed$$

$$shaftSpeed = \frac{60}{pulseIntervalMean \cdot driveRatio}$$

$$resampleRate = \frac{shaftSpeed}{60} \cdot pointsPerRev$$

$RS$ = residual data, $A1$ = signal average,

-continued $$signalAverageL1 = \frac{P2p(AI)}{\text{Rms}(AI)}$$

$FF = FFT$ of the signal average, $$shaftOrder_j = \sqrt{FF_j}, j = 1..3$$

$$gearDistFault = \frac{Stdev(RS)}{Stdev(AI)}$$

As described elsewhere herein, gearDistFault (GDF) is an effective detector for distributed gear faults such as wear and multiple tooth cracks, and is a complement of the indicator signalAverageL1 (also known as gearLocalFault).

In addition to the specifically referenced vectors below, the SI algorithm takes input from the indexer zero-crossing vector (ZC) and may also use others and indicated above.

The following definitions for indicators may also be included in an embodiment in connection with the SI algorithm:
  shaftpath is defined for the shaft descriptor
  indexPath is the path of the shaft seen by the indexer used for signal averaging
  numPathPairs is the number of path pairs defined for shaftPath and indexPath
  pulsesUsed is the number of pulses used per revolution of the indexer shaft
  pulseIntervalMean is the mean of the zero-crossing (ZC) intervals
  pointsPerRev is the number of output points per revolution in the signal average, The Bearing Energy (BE) algorithm 376 performs an analysis to reveal the four bearing defect frequencies (cage, ball spin, outer race, and inner race frequencies) that usually modulate the bearing shaft frequency. As such, these four frequencies are calculated based on the measured shaft speed and bearing geometry. Alternatively, the four frequency ratios may be obtained from the bearing manufacturers. The energy levels associated with these four frequencies and their harmonics are calculated for bearing fault detection. They are:
  Cage Energy: the total energy associated with the bearing cage defect frequency and its harmonics. Usually it is detectable only at the later stage of a bearing failure, but some studies show that this indicator may increase before the others.
  Ball Energy: the total energy associated with the bearing ball spin defect frequency and its harmonics.
  Outer Race Energy: the total energy associated with the bearing outer race defect frequency and its harmonics.
  Inner Race Energy: the total energy associated with the bearing inner race defect frequency and its harmonics.
The Total Energy indicator gives an overall measure of the bearing defect energies.

In one embodiment, one or more algorithms may be used in determining a CI representing a score quantifying a difference between observed or actual test distribution data and a normal probability distribution function (PDF) or a normal cumulative distribution function (CDF). These one or more algorithms may be categorized as belonging to a class of algorithms producing CIs using hypothesis tests ("hypothesis testing algorithms") that provide a measure of difference in determining whether a given distribution is not normally distributed. These hypothesis testing algorithms produce a score that is used as a CI. The score may be described as a sum of differences between an observed or actual test distribution function based on observed data and a normal PDF or normal CDF. An algorithm may exist, for example, based on each of the following tests: Chi-Squared Goodness of fit (CS), Kolmogorov-Smirnov Goodness of fit (KS), Lilliefors test of normality, and Jarque-Bera test of normality (JB). Other embodiments may also include other algorithms based on other tests for normality, as known to those of ordinary skill in the art. The hypothesis tests compare the test distribution to the normal PDF, for example as with CS test, or the normal CDF, for example as with the KS and Lilliefor tests.

What will now be described is an example in which the CS test is used in determining a score with a test distribution of observed actual data. In this example, the test distribution of observed data forms a Gamma (5,20) distribution function, having and alpha value of 5 and a beta value of 20. The mean of this Gamma (5,20) distribution is alpha*beta having a variance of alpha*beta$^2$. The Gamma (5,20) distribution function is a tailed distribution which graphically is similar to that of a normal distribution.

Figure 19:
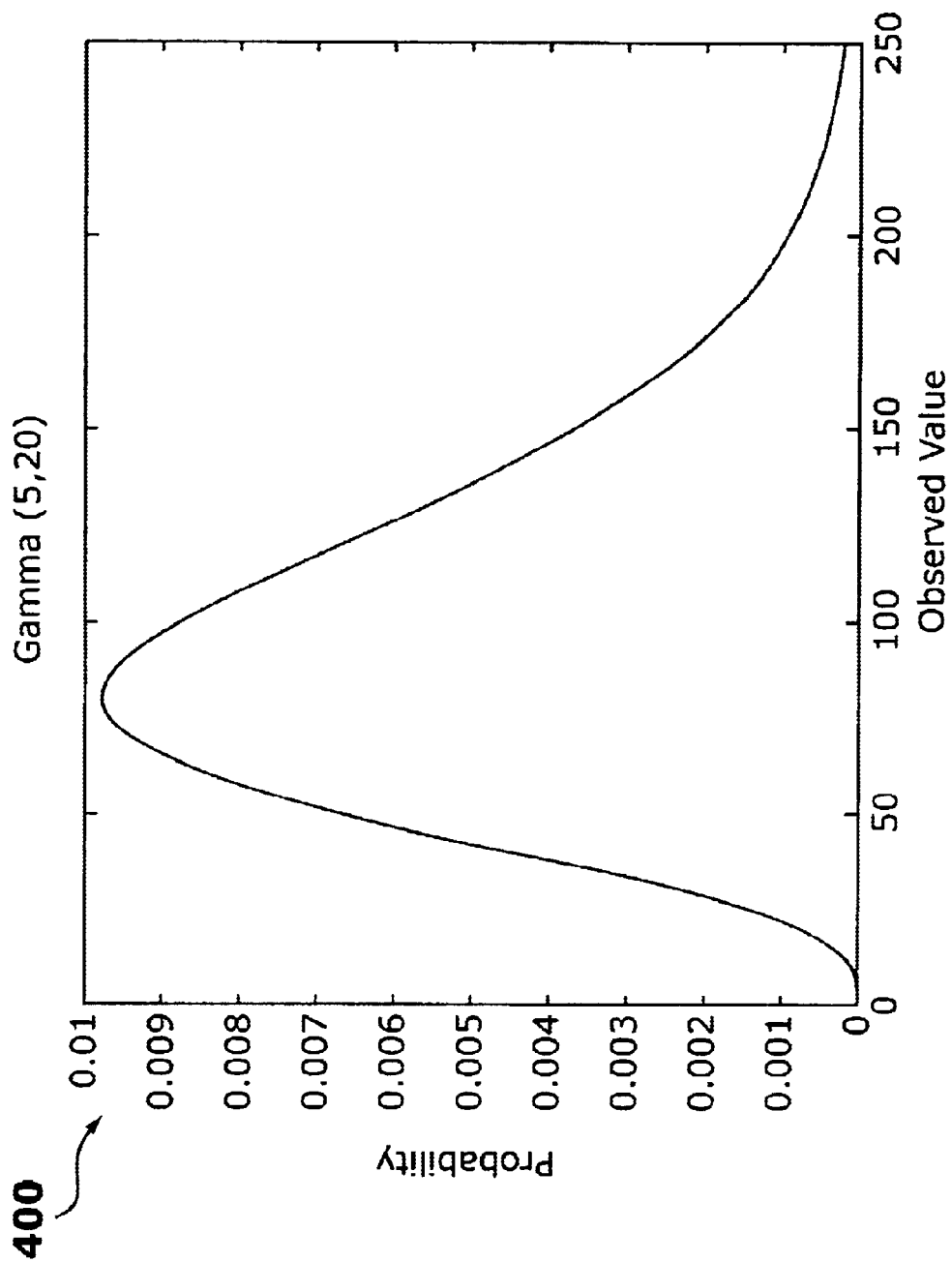
FIG. 19 is an example of a graphical representation of a probability distribution function (PDF) of observed data.

Referring now to FIG. 19, shown is an example of a graphical representation 400 of observed data.

Referring now to FIG. 20, shown is an example of a graphical representation 410 of the normal CDF and the Gamma (5,20) CDF of random data. Referring now FIG. 21, shown is an example of a graphical representation 420 of the difference between the normal CDF and the Gamma (5,20) CDF.

In one embodiment, if there are 1000 test samples used in forming a single CDF, the graphical representation, for example, in FIG. 21 represents differences in 1000 instances where the difference between the expected value (Normal CDF) and the maximum deviation of the (in this case defined as the score) observed gamma CDF can exceed some critical value. The critical value is that statistic which represents some predefined alpha error (the probability that the test indicates the distribution is not normal when in fact it is normal—this is typically set at 5%.) If the score exceeds the critical value, the distribution is said to be not normal statistic. The score is the maximum deviation from this statistic or alpha value.

It should be noted that the sensitivity or goodness of the test increases as the number of samples or instances (degrees of freedom "n") increases approximately as the square root of "n". For example, in the case where 1000 instances or samples are used such that n=1000, the sensitivity or ability of this CI to be used in detecting gear faults, for example, is roughly 31 times more powerful than kurtosis in identifying a non normal distribution.

Figure 22:
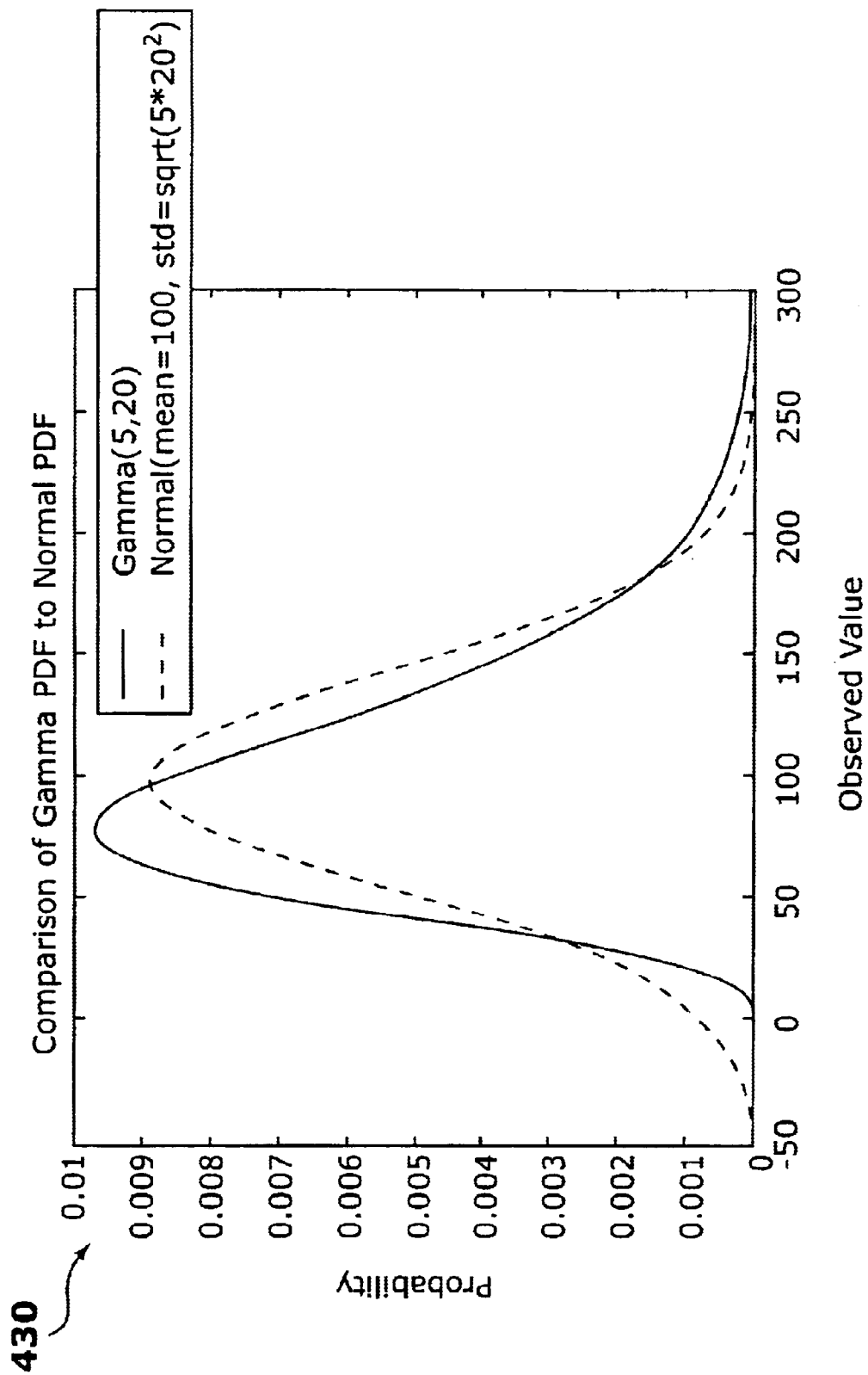
FIG. 22 is an example of a graphical representation of the PDF of observed data following a Gamma (5,20) distribution and a PDF of the normal distribution.

As another example, in the algorithm using the CS test, the normal PDF is used. Referring now to FIG. 22, shown is a graphical representation 430 of the normal PDF and the PDF of the Gamma (5,20) distribution. The representations of FIG. 22 are drawn as continuous lines rather than discrete intervals.

Figure 23:
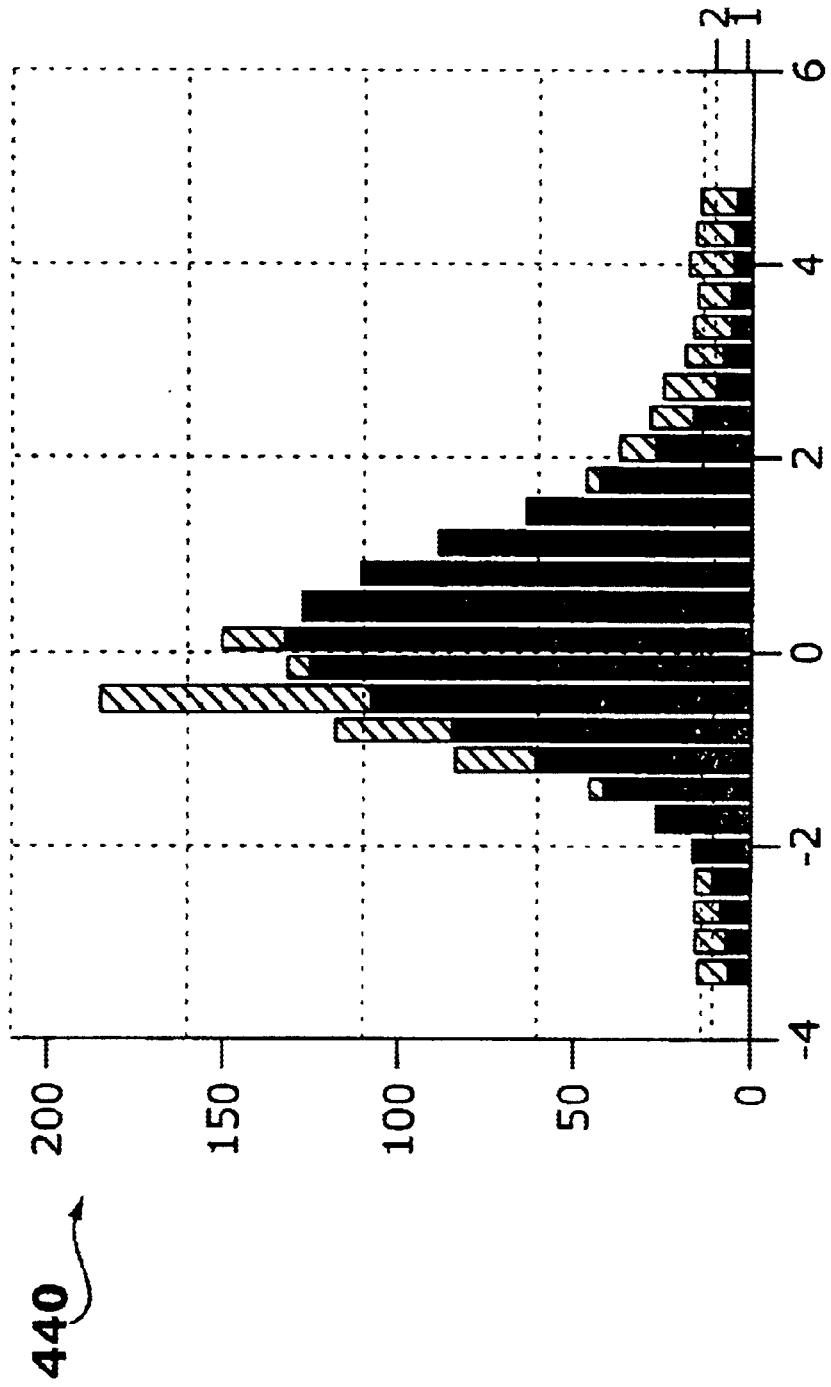
FIG. 23 is an example of another graphical representation of the two PDFs from FIG. 22 shown which quantities as intervals rather than continuous lines.

Referring now to FIG. 23, the quantities of the x-axis represented in FIG. 22 are shown in another representation 440 as being divided into discrete bins, intervals, or categories. For example, there may be 4 bins or intervals between any two integer quantities. Between 0 and 1, bin 1 includes values between [0,0.25), bin 2 includes values between [0.25, 0.50), bin 3 includes values between [0.050,0.75) and bin 4 includes values between [0.75, 1.0). For each bin, determine the number of observed and expected values, and their difference. Square each of the differences for each bin and then add all the differences and divide by the expected value for each bin. The CS test which sums all the differences for each category divided by the expected value for each category represented as:

$$\sum_{i=1}^{k} \frac{(fi-ei)^2}{ei}$$

for k categories or bins, k−1 degrees of freedom, fi is observed data and ei is expected data value or number in accordance with a normal distribution.

Figure 24A:
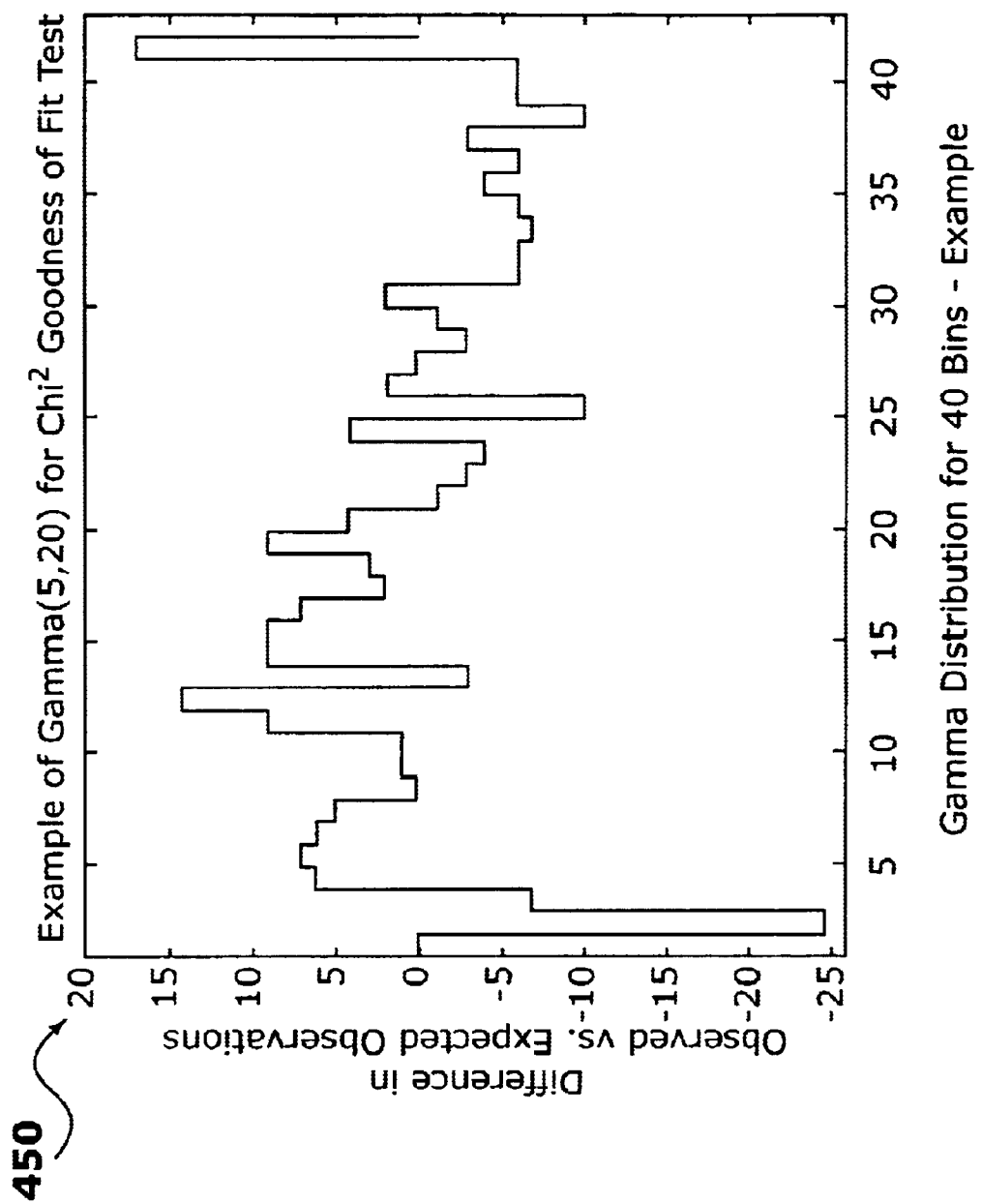
FIG. 24A is an example of a graphical representation of the differences between the two PDFs of observed data and the normally distributed PDF.

For each bin, take the difference between the observed and expected observation. Square this value and divided by expected number of observation. Sum over all bins. The statistic, the critical value is the $\chi^2$ at k−1 degrees of freedom may be, for example, 90.72 which is much greater than the 0.05 alpha value of a $\chi^2$, which is 54.57 for 39 degrees of freedom or 40 categories/bins. Thus, the observed data in this example as indicated by the statistic is not normally distributed. FIG. 24A represents graphically a difference between observed and expected values for each bin or interval of FIG. 23.

It should be noted that the foregoing algorithms provide a way of measuring both the skewness and kurtosis simultaneously by comparing the PDF or CDF of the test distribution against the PDF/CDF of a standard normal distribution in which a score is used as a CI as described above.

As known to those of ordinary skill in the art, other algorithms belonging to the hypothesis testing class may be used in computing CIs. The particular examples, algorithms, and tests selected for discussion herein are representations of those that may be included in the general class.

What will now be described is another algorithm that may be used in determining a CI in an embodiment of the system of FIG. 1. This may be referred to as an impulse determination algorithm that produces a CI indicating an amount of vibration that may be used in detecting a type of fault. The impulse determination algorithm takes into account the physical model of the system. One type of fault that this technique may be used to detect is a pit or spall on either: gear tooth, inner bearing race, outer bearing race or bearing roller element. This technique uses a model designed to detect this type of fault where the model is based on knowledge of the physical system. For example, if there is a pit or spall on a bearing, this may produce a vibration on a first bearing which may further add vibrations to other components connected to or coupled to the bearing.

In one embodiment, a model can be determined for a particular configuration by using configuration data, for example. In one configuration, for example, a signal received at a sensor may be a superposition of gear and bearing noise that may be represented as a convolution of gear/bearing noise and a convolution of the Gear/Bearing signal with the gearbox transfer function. Given this, if one type of fault is a pit or spall on either a: gear tooth, inner bearing race, outer bearing race or bearing roller element, a model that is designed to look for this type of fault can take advantage of knowledge of the physical system.

The impulse determination algorithm uses Linear Predictive Coding (LPC) techniques. As known to those skilled in the art, LPC may be characterized as an adaptive type of signal processing algorithm used to deconvolute a signal into its base components. In the case of a pit/spall fault, the base signal components are an impulse train generated by the fault hitting a surface (e.g gear tooth with geartooth, inner race with roller element, etc) and the bearing/case transfer function. The bearing, gear and case have there own transfer functions. Convolution here is transitive and multiplicative. As such, LPC techniques may be used to estimate the total convolution function of the total vibration that may be produced.

For example, in this arrangement, the total amount of vibration representing the total impulse signal generated by a configuration may be represented as:

[impulse]$\otimes$f(Gear)$\otimes$f(Bearing)$\otimes$f(Case)=[impulse]$\otimes$
[f(Gear)$\otimes$f(Bearing)$\otimes$f(Case)]

in which $\otimes$ represents the convolution operation.

It should also be noted that convolution is a homomorphic system such that it is monotonically increasing and that logarithmic transformations hold. Thus the relationship of c=a*b also holds for Log c=Log a+Log b. A "dual nature" of convolution is used in following representations to equate operations using convolution in the time domain to equivalent multiplication operation in the frequency domain.

If "y" represents the total response of all elementary responses, and "h" represents the response of the system for a series of elementary input impulses "imp" such that y is the convolution of imp and h, then this may be represented as:

$$y=\text{imp}\otimes h$$

and then converting "y" and "h" each, respectively, to the frequency domain represented as "Y" and "H", as may be represented by the following:

$$Y=\Im(y), H=\Im(h)$$

taking the Fourier transform (FFT) of each where H represents the transfer function. The convolution in the time domain may be equated to a multiplication in the frequency domain represented as:

$$Y=IMP \cdot H$$

in which IMP is the Fourier transformation of imp into the frequency domain. Above, imp is in the time domain.

The convolution in the time domain is equivalent to multiplication in the Frequency Domain. Referring to the homomorphic property of convolution, it follows that:

$$\log(Y)=\log(IMP)+\log(H),$$

therefore $$\log(IMP)=\log(Y)-\log(H),$$

$$IMP=\exp(\log(Y)-\log(H))$$

and finally $$imp=\Im^{-1}(IMP)$$

Using the foregoing, the system transfer function "H" may be estimated for the Gear/Bearing and Case to recover the impulse response allocated with a Gear or Bearing pit/spall fault. The estimation of this transfer function "H" may be accomplished using Linear Predictive Coding (LPC) techniques. LPC assumes that the Transfer Function is a FIR filter, and as such, the auto-correlation of the time domain signal may be used to solve for the filter coefficients in a minimum sum of square error sense.

Using the LPC model, there is an impulse that is convoluted with a FIR filter, such that:

$$y[n]=a_1x[n-1]+a_2x[n-2]+a_3x[n-3]+\ldots$$

LPC techniques may be used to estimate the coefficients a=($a_1$ . . . an) for an order p in a minimum sum of square error sense, n=p+1. The standard least squares error estimators may be used, wherein y=y[1, 2, ... n], and x is the time delayed signal, in which:

$$x = \begin{bmatrix} x[n-1, & n-2, & \ldots & n-p] \\ x[n-2, & n-3, & & n-p-1] \\ \vdots & \vdots & & \end{bmatrix}$$

where $a=(x^T x)^{-1} x^T y$. These values for a1 ... an may be used with the following equation:

$y_{hat}=ax$, $b=(y-y_{hat})^2$ and the estimator of error B is: $\Sigma_{all} b$.

Y may also be expressed as:

$Y=FFT(y[1, 2, \ldots n])$ in which y[1 ... n] are values in the time domain expressed in the frequency domain as a Fourier transform of the time domain values. Y represents current time vector measurements in the frequency domain.

In terms of a and B, the transfer function H may be estimated and represented as a/B, (freq. Domain). Note that "a" is a vector of the values a1 ... an obtained above.

The homomorphic property of convolution as described above may be used to estimate the impulse as represented in:

$IMP=\exp(\log(Y)-\log(H))$ *IMP Equation*

If there is no fault, the impulse, for example, may be characterized as "white noise". As the fault progresses, the impulse or the value of H becomes larger. The CI is the power spectral density at a bearing passing frequency for a bearing fault, or a mesh frequency for a gear fault. Other CIs based on the foregoing value may be a "score" of the Lilifers test for normality, or other such test.

In the foregoing, a pit or spall may cause a vibration or tapping. Subsequently, other elements in contact with the ball bearing may also vibrate exhibiting behavior from this initial vibration. Thus, the initial vibration of the pit or spall may cause an impulse spectrum to be exhibited by such a component having unusual noise or vibration.

The value of IMP as may be determined using the IMP Equation above represents the impulse function that may be used as a "raw" value and at a given frequency and used as an input into an HI determination technique. For example, the IMP at a particular frequency, since this the spectrum, determined above may be compared to expected values, such as may be obtained from the stored historic data and configuration data. An embodiment may also take the power spectrum of this raw impulse spectrum prior to being used, for example, as input to an HI calculation where the power spectrum is observed at frequencies of interest, such as the inner race frequency. For example, if the impulse function is within some predetermined threshold amount, it may be concluded that there is no fault.

Figure 24B:
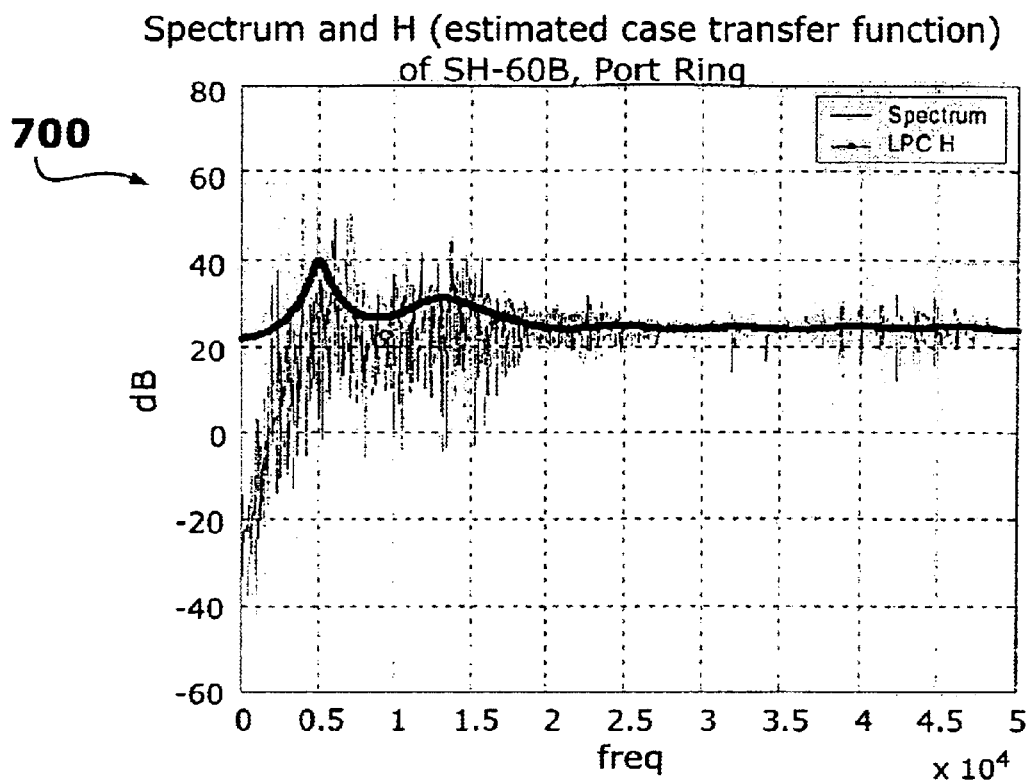
FIGS. 24B–24D are examples of a graphical data displays in connection with a healthy system.
Figure 24C:
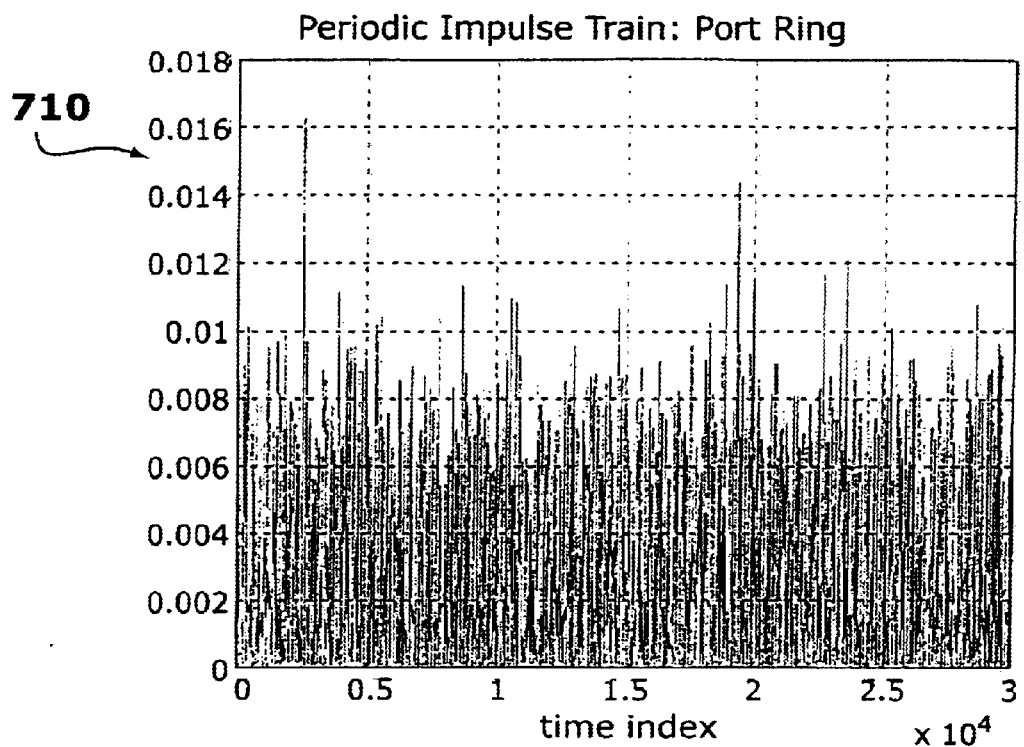

What is shown in the FIG. 24B and FIG. 24C are relative to a healthy system, such as a main gearbox, for example, such as in connection with a planetary race fault of an SH-60B U.S. Navy Helicopter built by Silorsky.

The FIG. 24B representation 700 shows an impulse train in the frequency domain of the healthy system.

It should be noted that an embodiment may estimate the transfer function H using LPC using different techniques. An embodiment may estimate the transfer function H using an autocorrelation technique(AutoLPC). An embodiment may also estimate the transfer function H using a covariance technique (CovLPC). Use of autocorrelation may use less mathematical operations, but require more data than using the covariance. Alternatively, use of the covariance technique may use more mathematical operations but require less data. As the amount of available data increases, the autocorrelation LPC result converges to the covariance LPC result. In one example, data samples are at 100 KHz with 64,000 data points used with the autocorrelation technique due to the relatively large number of data points.

FIG. 24C representation 710 shows the data of 700 from FIG. 24B in the time domain rather than the frequency domain.

Figure 24D:
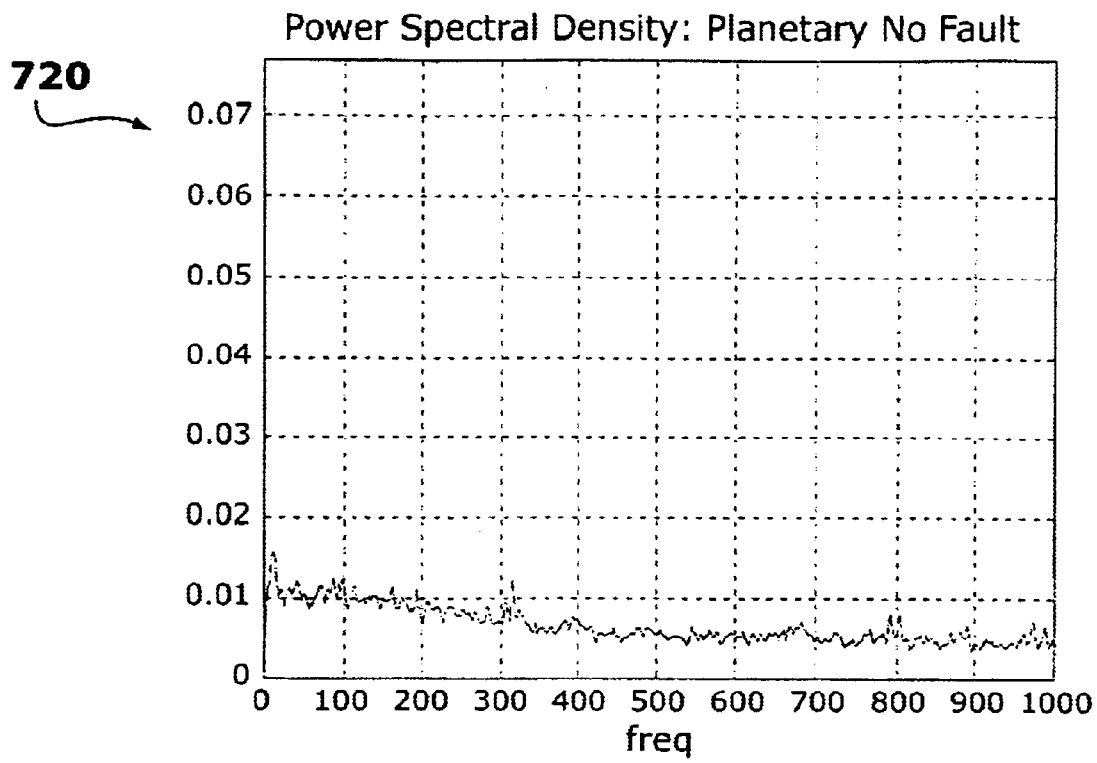

FIG. 24D representation 720 shows the power spectral density of the above figures as deconvolved time data of frequency v. dB values in a healthy system.

The foregoing FIGS. 24B–24D represent data in a graphical display in connection with a healthy system. Following are three additional graphical displays shown in FIGS. 24E–24G in connection with an unhealthy system, such as a starboard ring channel which exhibit data that may be expected in connection with a pit or spall fault.

Figure 24E:
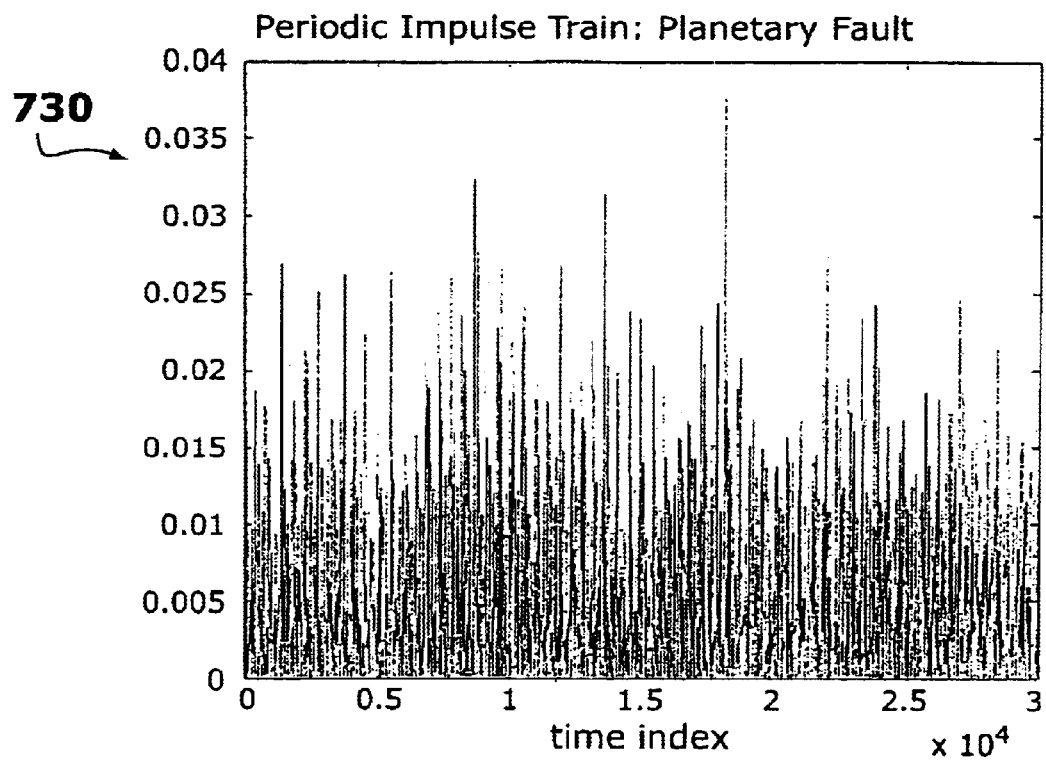
FIGS. 24E–24G are examples of graphical data displays in connection with a system having a fault.
Figure 24F:
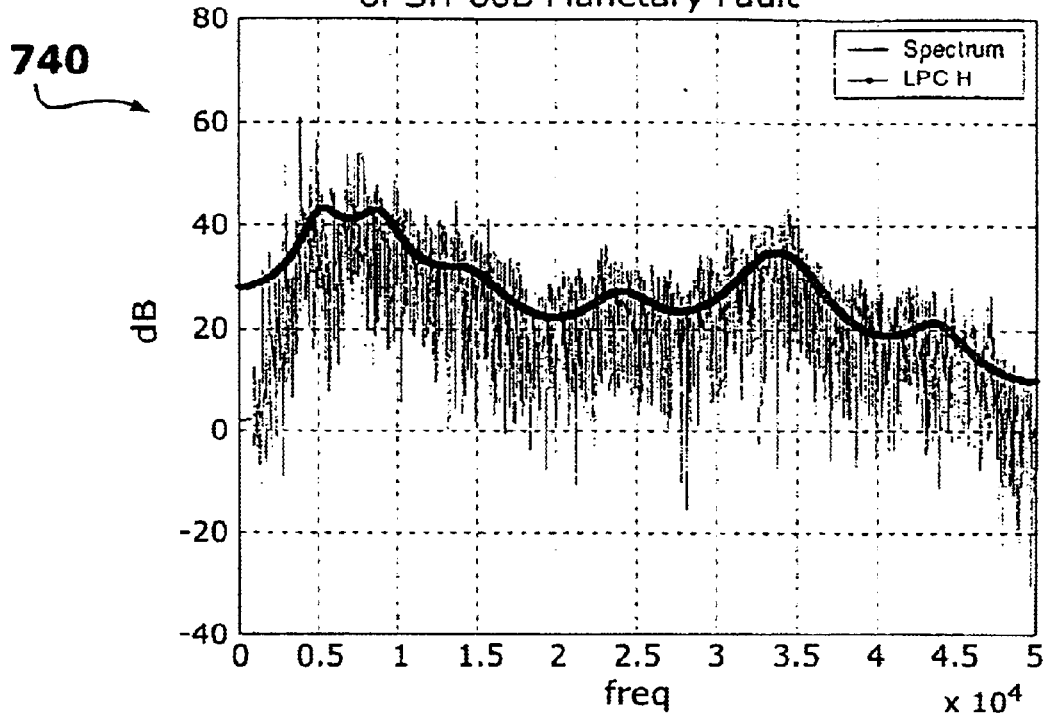

FIG. 24E, representation 730, illustrates an impulse train as may be associated with an unhealthy system in the time domain. FIG. 24F, representation 740, illustrates a graphical display of the impulse train in the frequency domain.

Figure 24G:
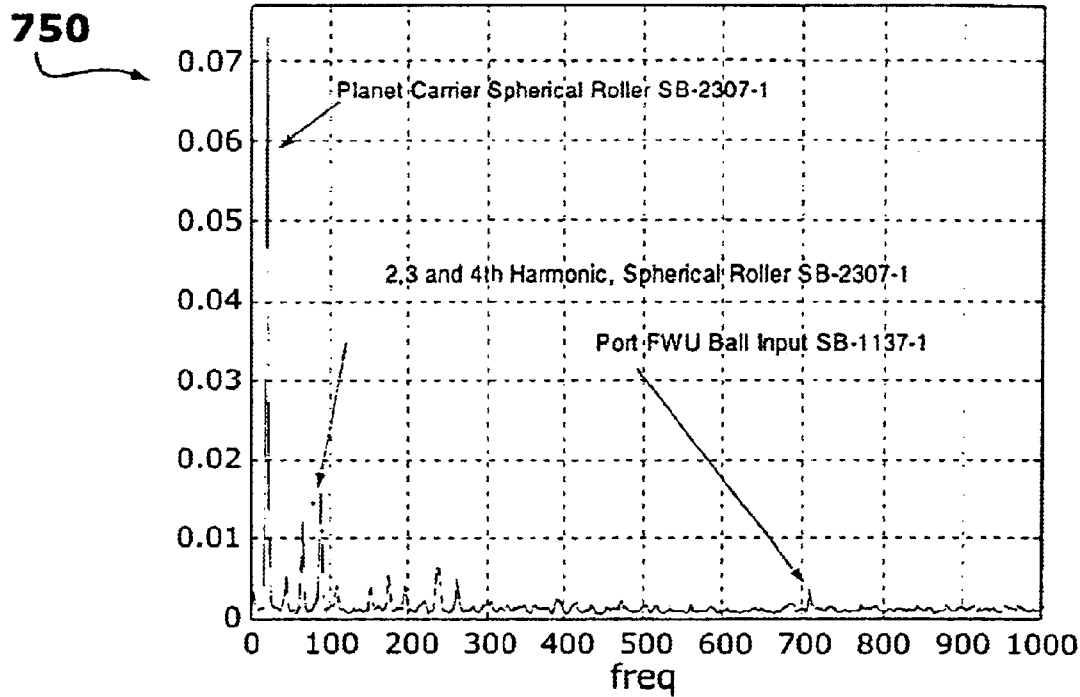

In FIG. 24G, shown is an illustration 740 is a graphical representation of the power spectrum of the impulse train represented in connection with the other two figures for the unhealthy system identified by a period impulse train associated with an inner race bearing fault. In this example, a spike may be viewed in the graphical display as well as the harmonics thereof.

It should be noted that other algorithms and CIs in addition to those described herein may be used in producing CIs used in techniques in connection with HIs elsewhere herein.

Figure 25:
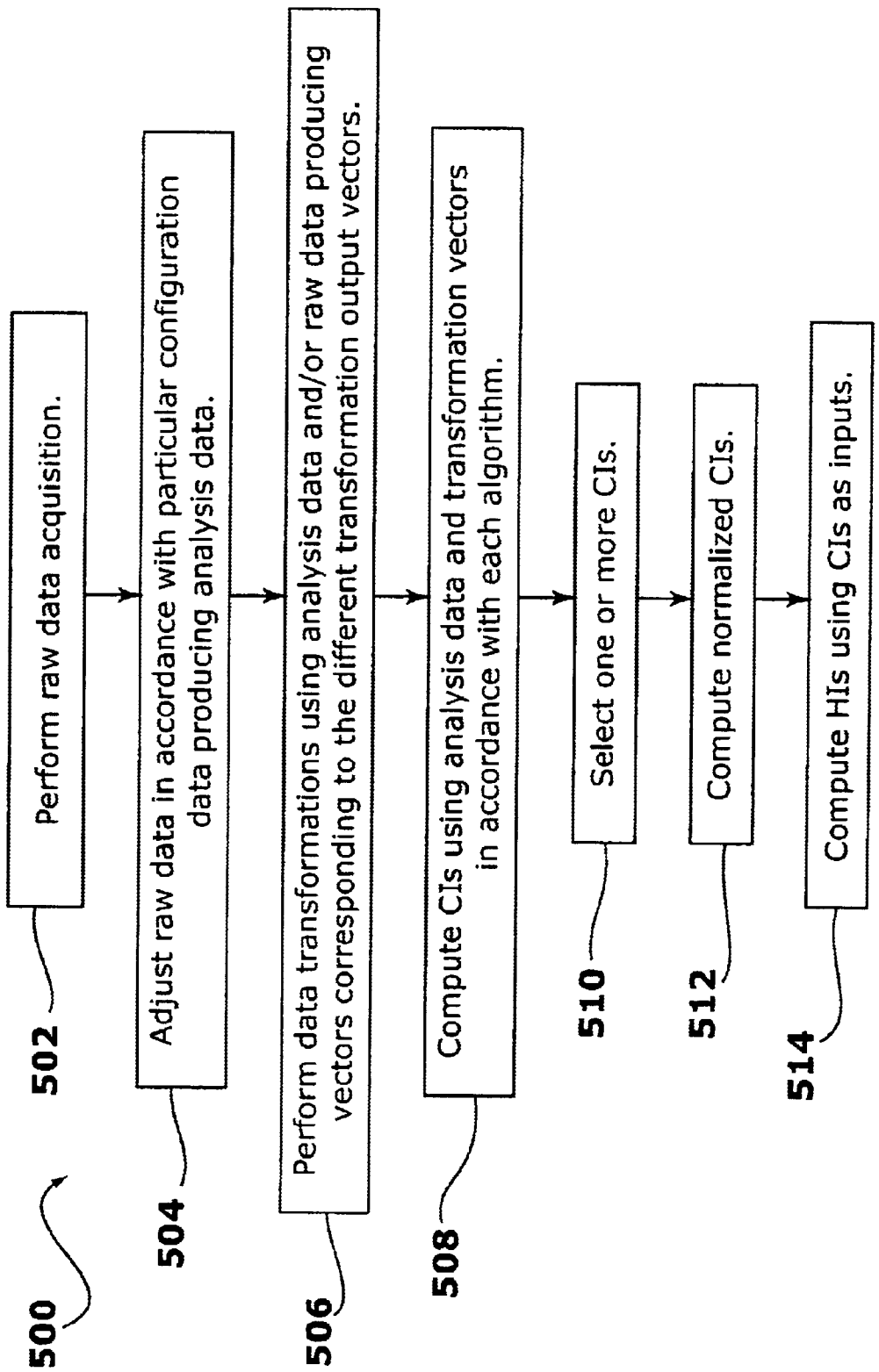
FIG. 25 is a flowchart of steps of one embodiment for determining health indicators (HIs)

What will now be described is one embodiment in which these CIs may be used. Referring now to FIG. 25, shown is a flow chart of steps of one embodiment for determining the health of a part as indicated by an HI. At step 502, raw data acquisition is performed. This may be, for example, issuing appropriate commands causing the VPU to perform a data acquisition. At step 504, the raw data may be adjusted, for example, in accordance with particular configuration information producing analysis data as output. It is at step 504, for example, that an embodiment may make adjustments to a raw data item acquired as may be related to the particular arrangement of components. At step 506, data transformations may be performed using the analysis data and other data, such as raw data. The output of the data transformations includes transformation output vectors. At step 508, CIs are computed using the analysis data and transformation vector data as may be specified in accordance with each algorithm. At step 510, one or more CIs may be selected. Particular techniques that may be included in an embodiment for selecting particular CIs is described elsewhere herein in more detail. At step 512, CIs may be normalized. This step is described in more detail elsewhere herein. At step 514, the selected and normalized CIs are used in determining HIs. Particular techniques for determining HIs are described in more detail elsewhere herein.

In an embodiment, due to the lengthy processing times, for example, in executing the different algorithms described herein, HI computations may not be executed in real time. Rather, they may be performed, for example, when a command or request is issued, such as from a pilot or at predetermined time intervals.

The hardware and/or software included in each embodiment may vary in one embodiment, data acquisition and/or computations may be performed by one or more digital signal processors (DSPs) running at a particular clock speed, such as 40 MHz, having a predetermined numerical precision, such as 32 bits. The processors may have access to shared memory. In one embodiment, sensors may be multiplexed and data may be acquired in groups, such as 8. Other embodiments may vary the number in each group for data sampling. The sampling rates and durations within an acquisition group may also vary in an embodiment. Data may be placed in the memory accessed by the DSPs on acquisition. In one embodiment, the software may be a combination of ADA95 and machine code. Processors may include the VPU as described herein as well as a DSP chip.

What will now be described are techniques for normalizing CIs in connection with determining HIs providing more detailed processing of step 512 as described in connection with flowchart 500.

Transmission error (T.E.) depends upon torque. Additionally, vibration depends upon the frequency response of a gear. As such, the CI, which also depends upon T.E. and vibration, is a function (generally linear) of torque and rotor speed (which is frequency), and airspeed as this may change the shape of the airframe. Thus, techniques that may be used in connection with determining the "health state" or HI of a component may normalize CIs to account for the foregoing since HIs are determined using CIs.

For each bearing, shaft and gear within a power train, a number of CIs may be determined. An embodiment may compare CI values to threshold values, apply a weighting factor, and sum the weighted CIs to determine an HI value for a component at a particular time. Because data acquisitions may be made at different torque (e.g. power setting) values, the threshold values may be different for each torque value. For example, an embodiment may use 4 torque bands, requiring 4 threshold values and weights for each CI. Additionally, the coarseness of the torque bands will result in increased, uncontrolled system variance. Alternatively, rather than use multiple threshold values and have an uncontrolled variance, an embodiment may use a normalization technique which normalizes the CI for torque and rotor RPM (Nr), and airspeed, expressed as a percentage, for example, in which a percentage of 100% is perfect. Use of these normalized CIs allows for a reduction of configuration such that, for example, only one threshold is used and variance may also be reduced.

The normalization technique that will now be described in more detail may be used in connection with methods of HI generation, such as the non-linear mapping method and the hypothesis testing method of HI generation that are also described in more detail elsewhere herein.

It should be noted that a deflection in a spring is linearly related to the force applied to the spring. The transmission may be similar in certain aspects to a large, complex spring. The displacement of a pinion and its corresponding Transmission Error (T.E.) is proportional to the torque applied. T.E. is a what causes vibration, while the intensity of the vibration is a function of the frequency response ($N_r$), where frequency is a function of RPM. Thus, vibration and the corresponding CI calculated using a data acquisition are approximately linearly proportional to torque, $N_r$ (over the operating range of interest) and/or airspeed although at times there may be a linear torque*Nr interaction effect. For example, gear box manufacturers may design a gearbox to have minimum T.E. under load, and a graphical representation of T.E. vs. Torque is linear, or at least piece wise linear. It should be noted that test data, for example used in connection with a Bell helicopter H-1 loss of lube test, shows a relationship between CI and torque suggesting linearity. Additionally, tests show that airspeed is also relevant factor. Other embodiments may take into account any one or more of these factors as well as apply the techniques described herein to other factors that may be relevant in a particular embodiment or other application although in this example, the factors of torque, airspeed and Nr are taken into account.

An equation representing a model minimizing the sum of square error of a measured CI for a given torque value in a healthy gear box is:

$$CI = B_0 + B_1 * \text{Torque} + B_2 Nr + B_3 \text{Airspeed} + T.E \quad \text{(Equation 1)}$$

The order of the model may be determined by statistical significance of the coefficients of Equation 1. In the previous equation, the T.E. of a "healthy" component may have, for example, a mean of zero (0) with some expected variance. It should be noted that if the model fits well for the lower order. Higher order coefficients are not required and may actually induce error in some instances. The following example is built as a first order model, higher orders may be solved by extension of that explained in the first order model. This model, written in matrix format is: y=B x where $$y = \begin{bmatrix} CI_1 \\ CI_{...} \\ CI_n \end{bmatrix} \quad B = [B_0 \; B_1 \ldots B_n] \text{ and } x = \begin{bmatrix} 1 & t_1 & N_{R_1} & \text{Airspeed1} \\ 1 & t_{...} & N_{R_{...}} & \text{Airspeed...} \\ 1 & t_n & N_R n & \text{Airspeed} n \end{bmatrix}$$

Each of the CIs included in the vector y is a particular recorded value for a CI from previous data acquisitions, for example, as may be stored and retrieved from the collected data 18. Also stored with each occurrence of a CI for a data acquisition in an embodiment may be a corresponding value for torque (t), Nr, and Airspeed. These values may also be stored in the collected data 18.

The model coefficients for B may be estimated by minimizing the sum of square error between the measured CI and the model or estimated CI using the observed performance data Solving the foregoing for the unbiased estimator of $B = (x^T x)^{-1} x^T y$. The variance of B is: $\text{Var}(B) = E(b-B)(b-B)^T = \sigma^2 (x^T x)^{-1}$ where b is an unbiased estimator of B. The unbiased estimator of $\sigma^2$ is $s^2$:

$$s^2 = \frac{e^T e}{n - p - 1} = \frac{(y - \hat{y})^T (y - \hat{y})}{n - p - 1} = \frac{y^T y - b^T x^T y}{n - p - 1}$$

In the vector B from y=xB, coefficient $B_0$ represents the mean of the data set for a particular component which, for example, may be represented as an offset value. Each of the other values B1 . . . Bn are coefficients multiplied by the corresponding factors, such as airspeed, torque, and Nr.

The foregoing B values or coefficients may be determined at a time other than in real-time, for example, when flying a plane, and then subsequently stored, along with corresponding X information, for example, in the collected data store 18. These stored values may be used in determining a normalized CI value for a particular observed instance of a CIobs in determining an HI. The normalized CI may be represented as:

$$CI_{normalized} = T.E. = CI\text{obs} - (B * x)$$

where CIobs represents an instance of a CI being normalized using previously determined and stored B and x values. Threshold values, as may be used, for example, in HI determination, may be expressed in terms of multiples of the standard deviation Warning=$B_0+3*\sigma^2(x^t x)^{-1}$, Alarm=$B_0+6*\sigma^2(x^t x)^{-1}$. It should be noted that a covariance that may be determined as:

$$\Sigma = s^2(x^t x)^{-1} \text{ where } s^2 \text{ is calculated as noted above.}$$

As described elsewhere herein, the foregoing techniques are based upon a healthy gear characterized as having noise that is stationary and Gaussian in which the noise approximates a normal distribution.

What will now be described are techniques that may be used in determining an HI using the normalized CI values as inputs. In particular, two techniques will be described for determining an HI. A first technique may be referred to as the non-linear map technique. The second technique may be referred to as the hypothesis test method of HI generation. It should be noted that CI values other than normalized CI values may be used in connection with HI determination techniques described herein.

It should be noted that an embodiment may use CI values that are not normalized in connection with the HI determination techniques described herein. In this instance, multiple torque bands may be used, one for each CI or group of CIs belonging to different torque bands. Additionally, a larger covariance matrix may be used as there may be a larger variance causing decrease in separation between classes.

For any generic type of analysis (gear, bearing, or shaft), a subset of the diagnostics indicators or CIs is selected. The CIs which are best suited to specify the fault indication may be developed over time through data analysis. Faults may be calculated at the component level and an HI may be calculated for a given component. If there is a component fault, then there is a sub-assembly fault, and therefore a drive train fault.

Following is a description of a non-linear mapping methodology for determining an HI. Given a set of component indicators I1, I2, I3, . . . IN, choose the desired subset of K indicators such that K<=N. For the chosen group of indicators, let WTi define the weight of the ith indicator, Wi the warning threshold, and Ai the alarm threshold. Then apply the following processing to the set of chosen indicators.

Heath Indicator Contribution Description for XX=1:K/*cycle through all K indicators in subset */
   If I[XX]<Wi/*if less than warning level Wi, assign 0*/
      Hi contribution=0
   elseif Wi*Ii<Ai
      Hi contribution=1*Wi
   else
      Hi contribution=2*Wi.
   end
end In the foregoing pseudo-code like description, each indicator or CI is weighted and contributes a portion to the HI determination. Subsequently all the Hi contributions for the selected CIs are summed and may be compared to threshold values for determining one of two possible outcomes of "healthy" or "not healthy".

Consider the following example table of information for a selected subset of 9 CIs along with threshold and weight values. It should be noted that in an embodiment, any one or more of the values for weights, warning and alarm values may be modified.

| CI No. | Value | Warning Level | Alarm Level | Weight | HI contribution |
|---|---|---|---|---|---|
| I2 | 3.26 | 3.5 | 4.0 | 1.0 | 0.0 |
| I3 | 3.45 | 3.0 | 3.5 | 1.0 | 1.0 |
| I6 | 7.5 | 6.0 | 8.0 | 1.4 | 1.4 |
| I9 | 0.88 | 0.5 | 0.75 | 0.9 | 1.8 |
| I14 | 4.2 | 3.5 | 4.5 | 1.0 | 1.0 |
| I17 | 4.7 | 3.5 | 4.5 | 0.9 | 1.8 |
| I22 | 5.2 | 2.0 | 4.0 | 1.1 | 2.2 |
| I23 | 4.4 | 3.5 | 4.5 | 1.2 | 1.2 |
| I24 | 18.9 | 10.0 | 20.0 | 1.0 | 1.0 |

Using the foregoing example and values, the sum of the HI contributions is 11.4. Applying the Health Indicator Contribution technique as set forth in the foregoing pseudo-code like description, I2, with a value of 3.26, is below the warning threshold, so the contribution to the index is 0. Indicator I3 has a value of 3.45, which contributes a 1 toward the index since the weight value is also 1. However, Indicator I6 contributes a 1.4 to the index because it crosses the warning level (contributing a value of 1 to the index) while being weighted by a factor of 1.4.

In the foregoing example, if no indicators were in alarm, the sum of HI contributions would be zero and if all indicators were in alarm, the sum would be 19, the worst fault case represented by this detector scheme. The HI may be represented as a value of 1 for healthy and 0 for not healthy as associated with a component represented by the foregoing CI values.

The HI may be determined by dividing 11.4/19, the maximum of worst case outcome to obtain 0.6. This overall health index output ratio can then be compared to another final output threshold, where normal components produce HIs, for example, less than 0.5; values between 0.5 and 0.75 represent warning levels, and values over 0.75 represent alarm.

It should be noted that the weights may be determined using a variety of different techniques. The weights of each CI may be determined using any one or more of a variety of techniques. One embodiment may determine weights for the CIs as:

$$\frac{1}{\sqrt{\text{eigen\_values\_of\_the\_covariance\_matrix}}}$$

It should be noted that other threshold values may be used in HI determination and may vary with each embodiment.

In one embodiment, using the normalized CI described elsewhere herein with the non-linear mapping technique, the threshold values may be represented as: Warning=$B_0+3*\sigma^2(x^t x)^{-1}$, Alarm=$B_0+6*\sigma^2(x^t x)^{-1}$, where $B_0$ may represent a mean or average coefficient as included in the B vector being solved for in the equations described in connection with CI normalization. In the foregoing example, the Warning threshold is 3 standard deviations and the Alarm level is 6 standard deviations. It should be noted that other threshold values may be used in and may vary in accordance with each embodiment.

What will now be described is a second technique that may be used in determining HIs using CIs, in particular, using normalized CIs.

The technique for HI determination may be referred to as Hypothesis testing technique for HI determination which minimizes the occurrence of a false alarm rate, or incorrectly diagnosing the health of a part as being included in the alarm classification when in fact the part is not in this particular state. In one embodiment, three classes of health indication may be used, for example, normal, warning and alarm classifications with alarm being the least "healthy" classification. Other embodiments may use the techniques described herein with a different number of classes. As described elsewhere herein, the class of a part indicating the health of the part may be determined based on measured vibrations associated with the part. Additionally, the technique described herein may use a transformation, such as the whitening transformation to maximize the class distributions or separation of values thus decreasing the likelihood or amount of overlap between the classes. In particular, this maximization of class separation or distance attempts to minimize the misclassification of a part. A description of the whitening transformation used in herein in following paragraphs may be found, for example, in "Detection, Estimation and Modulation Theory", Harry L. Van Trees, 1968, John Wiley & Sons, New York Library of Congress Catalog Card Number 67-23331.

Using the Hypothesis Testing method of HI generation, the HI or classification h(X) of a vector of normalized CI values denoted as X may be determined in which, as discussed elsewhere herein in more detail, X may be normalized Using the hypothesis testing technique, a determination is made as to which class (normal, warning or alarm) X belongs. In our instance, there are three classes. However, a first determination using the hypothesis testing may be performed using a first class corresponding to normal, and a second class corresponding to not normal. If the determination is normal, then testing may stop. Otherwise, if determination is made that the testing results are "not normal", a further or second determination using the hypothesis testing may be performed to determine which "not normal" class (alarm or warning) X belongs. Thus, the hypothesis testing technique may be performed more than once in accordance with the particular number of classes of an embodiment. For three classes, there are two degrees of freedom such that if the sample X is not from A or B classes, then it is from Class C.

X may belong to class $\omega_1$ or $\omega_2$, such that:

$$q_1(X) \underset{\omega_2}{\overset{\omega_1}{<>}} q_2(X)$$

(the notation $$\underset{\omega_2}{\overset{\omega_1}{<>}}$$

means that if $q_1(X)$ is greater than $q_2(X)$, choose class 2, $\omega_2$, or if $q_1(X)$ is less than $q_2(X)$, choose class 1, $\omega_1$.) In the foregoing, $q_1$ is the a posteriori probability of $\omega_i$ given X, which can be computed, using Bayes theorem in which $q_i = P_i p_i(X)/p(X)$, where $p(X)$ is the mixed density function. The mixed density function is the probability function for all cases where $q_i$ is the unconditional probability of "i" given the probability of "i" conditioned on the mixed density function.

Substituting the foregoing representation of each q1 and q2, since p(X) is common to both, now:

$$P_1 p_1(X) \underset{\omega_2}{\overset{\omega_1}{<>}} P_2 p_2(X)$$

or as a likelihood as $$\ell(X) = \frac{p_1(X)}{p_2(X)} \underset{\omega_2}{\overset{\omega_1}{<>}} \frac{P_2}{P_1}.$$

The likelihood function ratio is a quantity in hypothesis test. The value $P_2/P_1$ is the threshold value. In some instances, it may be easier to calculate the minus log likelihood ratio. In this case, the decision rule becomes (e.g. now called the discriminate function):

$$h(X) = -\ln \ell(X) = -\ln p_1(X) + \ln p_2(X) \underset{\omega_2}{\overset{\omega_1}{<>}} \ln \frac{P_2}{P_1}$$

Assume that the $p_i(X)$'s are normally distributed with mean or expected values in vectors $M_i$, and covariance matrix $\Sigma_i$. This assumption may be determined without loss of generality in that, any non-normal distribution can be whitened, as with the whitening transformation described elsewhere herein, with the appropriate power transform, or by increasing the sample size to the point where the sample size is very large. Given this, the decision rule becomes:

$$h(X) = -\ln \ell(X) \quad \text{Equation E1}$$

$$= \frac{1}{2}(X - M_1)^T \Sigma_1^{-1}(X - M_1) - \frac{1}{2}(X - M_2)^T \Sigma_2^{-1}(X - M_2) + \frac{1}{2}\ln \frac{|\Sigma_1|}{|\Sigma_2|} \underset{\omega_2}{\overset{\omega_1}{<>}} \ln \frac{P_2}{P_1}$$

Recall that maximization of distance between the two classes is desired to minimize the chance of a false alarm or misclassification of a part as broken when it is actually normal.

A function Z is defined as Z=X−M, (e.g. a shift where X is the measured CI data and M is the mean CI values for a class), so that:

$d_z^2(z) = Z^T \Sigma^{-1} Z$ (this distance is the n dimensional distance between two distributions).

Note that $\Sigma$ represents the covariance. It may be determined that a particular Z maximizes the distance function, subject to $Z^T Z = I$, the identity matrix.

Using a standard Lagrange multiplier, $\mu$, to find the local extrema (e.g. the maximum) a partial derivative is obtained with respect to Z in the following:

$$\partial/\partial Z\{Z^T \Sigma^{-1} Z - \mu(Z^T Z - I)\} = 2\Sigma^{-1} Z - 2\mu Z$$

where $\Sigma$ is the eigenvector of X, which may then be set to zero to find the extrema and solving for Z:

$\Sigma^{-1} Z = \mu Z$ or $\Sigma Z = \lambda Z$ where $\lambda = 1/\mu$. In order that a non-null Z exits, $\lambda$ must be chosen to satisfy the determinant:

$|\Sigma - \lambda I| = 0$.

Note that $\lambda$ is the eigenvalue of X and $\Sigma$ is the corresponding eigenvector. $\Sigma$ is a symmetric n×n matrix (e.g. a covariance matrix), there are n real eigenvalues ($\lambda_1 \ldots \lambda_n$) and n real eigenvectors $\phi_1 \ldots \phi_n$. the characteristic equation is: $\Sigma\Phi=\Phi\Lambda$, and $\Phi^T\Phi=I$ where $\Phi$ is an n×n matrix consisting of n eigenvectors and $\Lambda$ is a diagonal matrix of eigenvalues (e.g. the eigenvector matrix and eigenvalue matrix, respectively).

Y, representing the coordinated shifted value of X, may be represented as:

$$Y=\Phi^T X,$$

having a covariance matrix of y, $\Sigma_y=\Phi^T\Sigma_x\Phi=\Lambda$ where $\Sigma_x$ represents the covariance of the vector of matrix x. Continuing, the whitening transformation may be defined such that:

$$Y=\Lambda^{-\frac{1}{2}}\Phi^T X=(\Phi\Lambda^{-\frac{1}{2}})^T X,\ \Sigma_y=\Lambda^{-\frac{1}{2}}\Phi^T\Sigma_x\Phi\Lambda^{-\frac{1}{2}}=\Lambda^{-\frac{1}{2}}\Lambda\Lambda^{-\frac{1}{2}}=I,$$

Thus the transformation that maximizes that distance between distribution or classes is:

$$A=\Lambda^{-\frac{1}{2}}\Phi^T \text{ as shown above.}$$

Using this value of A, define $$A^T\Sigma_1 A=I,\ A^T\Sigma_2 A=K,\text{ and }A^T(M_2-M_1)=L \text{ and}$$

$(\Sigma_1^{-1}\Sigma_2^{-1})^{-1}$ transformed to a diagonal matrix $\Lambda$ by A that may be represented as:

$$\Lambda=A^T[A(I-K^{-1})A^T]^{-1}A=(I-K^{-1})^{-1}$$

which may be substituted into the discriminate function defined above:

$$h(X)=\tfrac{1}{2}Y^T\Lambda^{-1}Y-[(-K^{-1}L)^T]Y+[-\tfrac{1}{2}L^T K^{-1}L-\tfrac{1}{2}\ln|K|-\ln P_2/P_1]$$

Thus, if the above is less than the threshold, for example, ln $P_2/P_1$), then the component is a member of the normal or healthy class. Otherwise, the component is classified as having an HI in the broken class, such as one of alarm or warning. In the latter case, another iteration of the hypothesis testing technique described herein may be further performed to determine which "broken" classification, such as alarm or warning in this instance, characterizes the health of the component under consideration.

In the foregoing technique for hypothesis testing, values, such as the a posteriori probabilities $q_1$ and $q_2$, may be obtained and determined prior to executing the hypothesis testing technique on a particular set of CI normalized values represented as X above. As known to those of ordinary skill in the art, Bayes theorem may be used in determining, for example, how likely a cause is given that an effect has occurred. In this example, the effect is the particular CI normalized values and it is being determined how likely each particular cause, such as a normal or broken part, given the particular effects.

It should be noted that operating characteristics of a system define the probability of a false alarm (PFA) and the probability of detection (PD). The transformation used to maximize the distance function optimizes the discrimination between classes. However, the threshold value selected given a discriminate function may be used in determining the PD and PFA. In some embodiments, the cost of a false alarm may be higher than the cost of a missed detection. In these instances, the PFA may be set to define threshold values, and then accept the PD (e.g., a constant false alarm rate (CFAR) type of process). The distance function is a normal density function, based on the conditional covariance of the tested values under consideration. Given that, the PFA may be determined as: $P_F=P(H_0 H_1)$, which means the probability that the sufficient statistic is greater than some threshold is the integral of the threshold to infinity of a normal PDF.

$$P_{FA}=\int_\alpha^\infty p_{l|H_0}(l|H_0)dL=\int_\alpha^\infty 1/2\pi\ \exp(-x^2/2)dx$$

where the lower integral limit of $\alpha=ln(P_1/P_2)/d+d/2$, and, as before $d^2=(M_2-M_1)^T\Sigma_1 31\ 1(M_2-M_1)$ In this example, the threshold may be the ln $(P_2/P_1)$. This integration is the incomplete gamma function. Conversely, the probability of a detection (PD) is:

$$P_D=\int_\alpha^\infty p_{l|H_1}(l|H_1)dL=\int_\alpha^\infty 1/2\pi\ \exp(-(d)^2/2)dx$$

but now $\alpha=-ln(P_2/P_1)/d+d/2$, and $d^2=(M_1-M_2)^T\Sigma_2^{-1}(M_1-M_2)$ Note, the distance function is relative to the condition (e.g. $H_0$ or $H_1$) being investigated.

Figure 26:
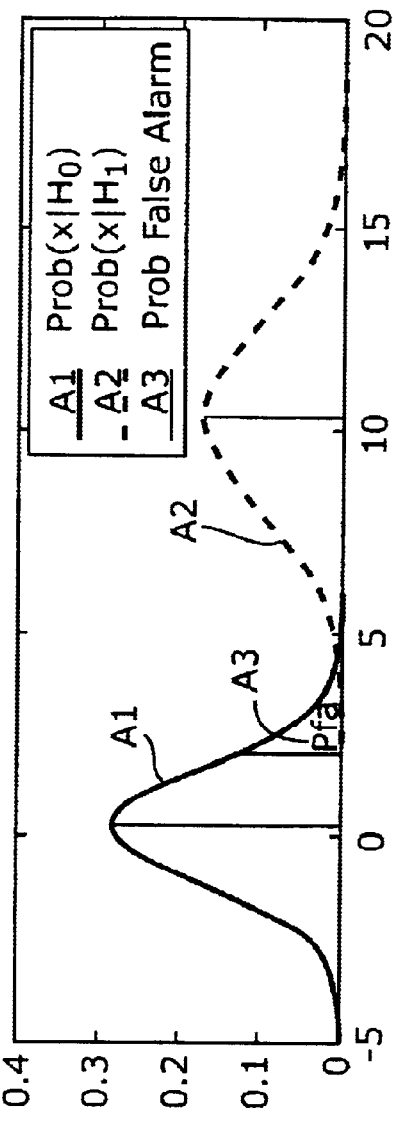
FIG. 26 is a graphical illustration of the probability of a false alarm (PFA) in one example.

Referring now to FIG. 26, shown is an example of a graphical illustration of the probability of a false alarm PFA represented by the shaded region A3 which designates the overlap between the distribution of class H0, denoted by the curve formed by line A1, and class H1, denoted by the curve formed by line A2.

Figure 27:
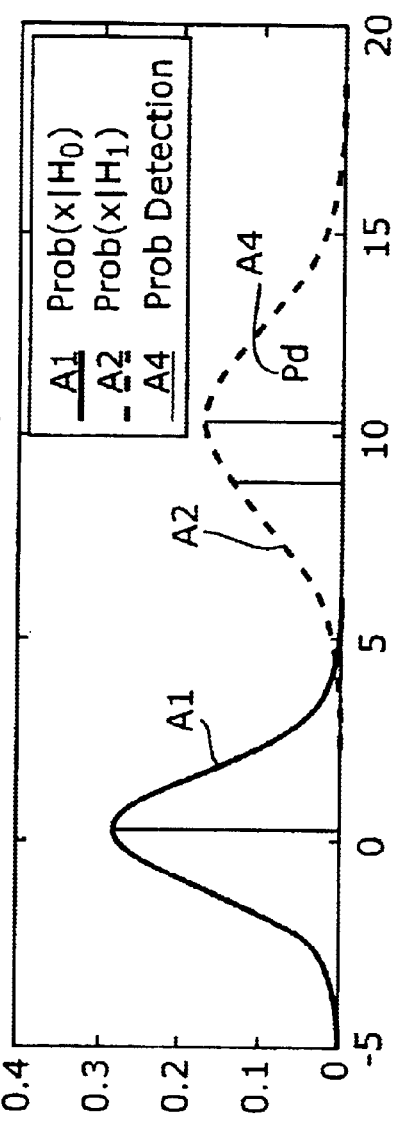
FIG. 27 is a graphical illustration of the probability of detection (PD) in one example.

Referring now to FIG. 27, shown is an example of a graphical illustration of the probability of an appropriate detection (PD) represented as area A4 as belonging to class represented by H1 as represented by the curve formed by line A2.

Figure 28:
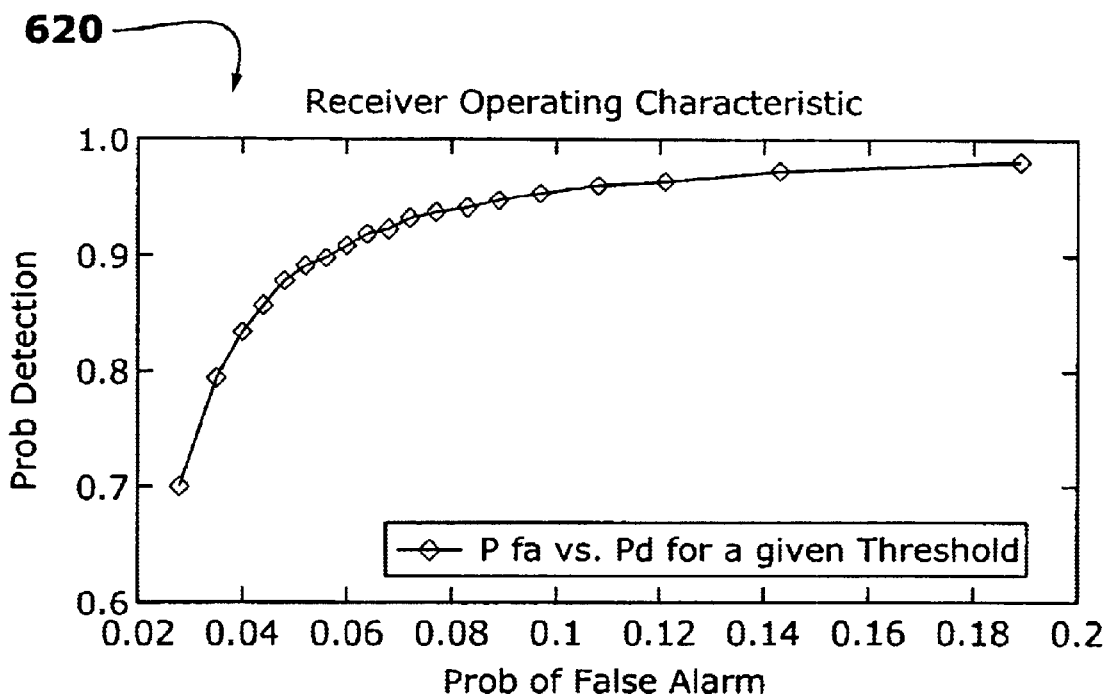
FIG. 28 is a graphical illustration of the relationship between PD and PFA and threshold values in one embodiment.

Referring now to FIG. 28, shown is a graphical illustration of a relationship in one embodiment between the PFA and PD and the threshold value. Note that as the threshold increases, the PD increases, but also the PFA increases. If the performance is not acceptable, such as the PFA is too high, an alternative is to increase the dimensionality of the classifier, such as by increasing the population sample size, n. Since the variance is related by 1/sqroot(n), as n increases the variance is decreased and the normalized distance between the distributions will increase. This may characterize the performance of the system. The likelihood ratio test used herein is a signal to noise ratio such that the larger the ratio, (e.g., the larger the distance between the two distributions), the greater the system performance. The process of taking an orthonormal transformation may be characterized as similar to the of a matched filter maximizing the signal to noise ratio.

Figure 29:
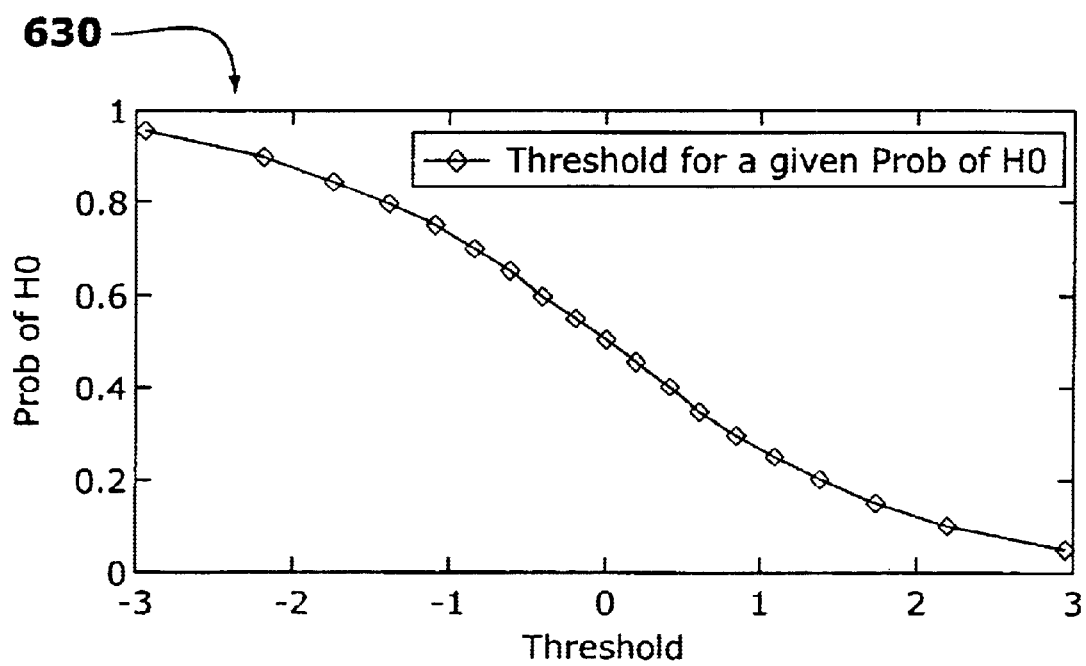
FIG. 29 is an graphical illustration of the probability of Ho and threshold values in one embodiment.

Referring now to FIG. 29, shown is an example of a graphical illustration of how the threshold may vary in accordance with the probability of determining class H0.

It should be noted that false alarm rate and detection rate are two factors that may affect selection of particular values, such as thresholds within a particular system. In the example embodiment described herein, false alarm rate is a determining factor, for example, because of the high cost associated with false alarms and the fact that they may corrode confidence when a real fault is detected. It should be noted that other embodiments and other applications may have different considerations. Further in this example of the system of FIG. 1, certain factors may be considered. An acceptable false alarm rate, for example, such as 1 false alarm per 100 flight hours, is established. An estimate of the number of collection opportunities per flight hours may be determined, such as four data collections. A number of HIs may be selected for the system, such as approximately 800. A confidence level may be selected, such as that there is a 90% probability that a false alarm rate is less than 1 per 100 flight hours.

In this example, it should be noted that each HI is a an independent classification event such that the law of total probability may give the system alarm rate using the foregoing:

System $PFA=1/(100*4*800)=3.1250*10^{-6}$.

It should also be noted that in the foregoing, when the covariance of two classes is approximately the same, or for example, unknown for a class, the logarithm likelihood ratio test for classification may be simplified in that the model may be reduced to a linear rather than quadratic problem having the following model:

$$(M_2 - M_1)^T \Sigma^{-1} X + \frac{1}{2}(M_1^T \Sigma^{-1} M_1 - M_2^T \Sigma^{-1} M_2) \underset{\omega_2}{\overset{\omega_1}{\lessgtr}} \ln \frac{P_2}{P_1}$$

If the covariance is whitened, the model simplifies further (assuming the appropriate transformation is made to the means and measured values).

$$(M_2 - M_1)^T X + \frac{1}{2}(M_1^T M_1 - M_2^T M_2) \underset{\omega_2}{\overset{\omega_1}{\lessgtr}} \ln \frac{P_2}{P_1}$$

What will now be described are techniques that may be used in connection with selecting a subset of CIs, such as selection of normalized CIs, for example, under consideration for use in determining a particular HI.

If we have a two or more classes (such as alarm, warning and normal classifications), feature extraction, or determining which CIs to use in this embodiment, may become a problem of picking those CIs or features that maximize class separability. Note that separability is not a distance. As described elsewhere herein, an eigenvector matrix transformation may be used in maximizing the distance between two functions or distribution classes. However, this same technique may not be applicable when some of the information (e.g. dimensionality) is being reduced. For example, in the following test case, three features, or CIs, are available, but only two are to be selected and used in determining HI classification. The distributions are:

$$Cov_1 = \begin{bmatrix} 1 & -.5 & .5 \\ -.5 & 2 & .8 \\ .5 & .8 & 2.5 \end{bmatrix}, M_1 = \begin{bmatrix} 0 \\ 0 \\ 0 \end{bmatrix}, Cov_2 = \begin{bmatrix} 1 & .7 & .7 \\ .7 & 2.5 & 1 \\ .7 & 1 & 2.5 \end{bmatrix}, M_2 = \begin{bmatrix} 3 \\ -1 \\ 3 \end{bmatrix}$$

When looking at the eigenvalues of the whitening transformation (1.9311, 3.0945, 0.4744), the maximum distance of the distribution is an axis y (e.g. $2^{nd}$ dimension, the distribution was whitened and the project dimension (e.g. x, y or z) was plotted), but this axis has the minimum separability. Using this as one of the two features will result in higher false alarm rates than another feature. This may identify the importance of feature selection in maximizing the separability.

The problem of separability may be characterized as a "mixed" problem in that differences in means may be normalized by different class covariance. If the mean values are the same, or the covariance are the same, techniques such as the Bhattacharyya Distance may be used to measure class separability. However, same mean or covariance values may not be likely and thus such techniques may not be applicable. Statistical tools developed in discriminant analysis may be used to estimate class separability.

A measure of within class scatter may be represented as the weighted average of the class covariance:

$$S_w = \sum_{i=1}^{L} P_i \Sigma_i,$$

for each class I, where Pi is the probability of the occurrence of the covariance $\Sigma_I$ for that class. In one embodiment, there may be two classes, such as healthy or unhealthy. When considering the unhealthy status, for example, when performing a second round of hypothesis testing described herein, there may be alarm and warning classes.

A measure of between class scatter, Sb, may be represented as the mixture of class means:

$$S_b = \sum_{i=1}^{L} P_i (M_i - M_0)(M_i - M_0)^T, M_0 = \sum_{i=1}^{L} P_i M_i.$$

Note that M0 represents the mean or expected value of the classes and Mi–M0 is a difference or variation from the expected value for the classes under consideration. The formulation for a criteria for class separability may result in values that are larger when the between class scatter is larger, or when the within class scatter is smaller. A typical criteria for this is $J=\text{diag}(S_w^{-1} S_b)$, where In general, $S_w$ is not diagonal. One technique takes the whitening transformation of $S_w$ where $A^T S_w A=I$, then define the whitening transformation of Sb as:

$$S_{bw}=A^T S_b A.$$

Now taking the diagonal of the foregoing Sbw gives a better representation of the class separability of each feature.

In summary, CIs may be selected in accordance with the technique described above to obtain and examine the diagonals of the "whitened" Sb, represented as Sbw. Let X be a matrix where rows and columns represent different CIs having a covariance matrix $\Sigma$. An embodiment may use normalized CIs and select a portion of these for use. An embodiment may also use CIs however, those selected should belong to the same torque band.

As described elsewhere herein, let A represent the corresponding eigenvalue matrix and $\Phi$ as the corresponding eigenvector matrix for the CI matrix X. Then, A, as described elsewhere herein in connection with the whitening transformation, may be represented as:

$$A=\Lambda^{-1/2}\Phi^T$$

where A is the transformation matrix that whitens the covariance $\Sigma$. If Sb is defined as above as the between mean covariance of the classes, the whitening matrix A may be used to normalize the differences and give a distance between the mean values of the different classes, such that $$Sbw=A^T Sb A$$

where Sbw represents the "whitened" Sb. The diagonals of Sbw may then be sorted in descending order in which each diagonal represents an approximation of the size of the separation between features or CIs. Thus, selection of a subset of "n" features or CIs from a possible "m" maximum CIs included in X may be determined by selecting the "n" largest diagonals of the matrix Sbw. In particular, the diagonal entry 1,1 corresponds to the first column of the covariance matrix and the first CI in the vector X, entry 2,2 to the second column of the covariance matrix and the second CI in the vector X being considered, and so on.

Once a particular HI is determined at a point in time, it may be desired to use techniques in connection with trending or predicting HI values of the component at future points in time. Techniques, such as trending, may be used in establishing, for example, when maintenance or replacement of a component may be expected. As described elsewhere herein, techniques may be used in determining an HI in accordance with a vector of CI values having expected CI values included in vector $M_i$ for a given HI classification, i, having a covariance matrix $\Sigma_i$. One technique uses a three state Kalman filter for predicting or trending future HI values.

The Kalman filter may be used for various reasons due to the particular factors taken into account in the embodiment and uses described herein. It should be noted that other systems embodying concepts and techniques described herein may also take into account other noise factors. In one embodiment, the Kalman filter may be preferred in that it provides for taking into account the noise of a particular arrangement of components. There may be noise corruption, such as indicated, for example, by the covariance matrices described and used herein. It may be desirous to filter out such known noise, such as using the Kalman filter, providing for smoothing of data values.

The Kalman filter provides a way to take into account other apriori knowledge of the system described herein. In particular, the health of a component, for example, may not change quickly with time. The difference between the health of a component at a time t, and time t+delta may not be large. This technique may also be used in connection with determining future HIs of a particular part, for example, where the part is old. A part may have reached a particular state of relatively bad health, but still a working and functional part. The techniques described herein may be used with an older part, for example, as well as a newer part.

In the arrangement with the Kalman filter, state reconstruction may be performed using the Ricatti equation, as known to those of ordinary skill in the art. The technique that is described herein uses a three-state Kalman filter of HI, and the first and second derivatives thereof with respect to changes in time, denoted, respectively, $dt^2$ and $dt^3$. The Ricatti equation in this instance uses a [1×3] vector of time values rather than a single value, for example, as may be used in connection with a single state Kalman filter. What will now be described are equations and values that may be used in determining a future value of a particular HI. Let:

$$H = [1\ 0\ 0]$$

$$\Phi = \begin{bmatrix} 1 & dt & dt^2/2 \\ 0 & 1 & dt \\ 0 & 0 & 1 \end{bmatrix}$$

$$Q = 2\sigma^2 \bar{t} \begin{bmatrix} dt^3/2 & dt^2/2 & \overline{t} \\ dt^2/2 & dt & 1 \\ \overline{t} & 1 & 1/\bar{t} \end{bmatrix}$$

$$X = \begin{bmatrix} \text{HI\_est} \\ \dot{H}I \\ \ddot{H}I \end{bmatrix}$$

in which:

σ is the power spectral density of the system,
R is the measurement error,
P is the covariance,
Q is the plant noise,
H is the measurement matrix,
K is the Kalman gain, and
Φ is the state transition matrix.

H may be characterized as the Jacobian matrix. Since the value of a single HI is desired, only the first entry in the H vector is 1 with remaining zeroes. There are n entries in the n×1 vector H for the n state Kalman filter. Similarly, the X vector above is column vector of 3 HI entries in accordance with the three-state Kalman filter. The end value being determined is the vector X, in this instance which represents a series of HI values, for which the first entry, HI_est in the vector X is the one of interest as a projected HI value being determined. Within the vector X, $\dot{H}I$ represents the first derivative of HI_est and $\ddot{H}I$ represents the second derivative of HI_est. $\bar{t}$ represents the average amount of time between measurements or updating of the HI value. In other words, if dt represents a measurement or delta value in units of time between HI determinations, and this is performed for several instances, $\bar{t}$ represents the average of the delta values representing time changes.

What will now be presented are equations representing the relationships between the above quantities as may be used in determining a value of X(1) for predicting or estimating an HI value at a future point in time given a current HI value.

$$X_{t|t-1} = \Phi X_{t-1|t-1} \quad \text{(Equation T1)}$$

$$P_{t|t-1} = \Phi P_{t-1|t-1} \Phi^T + Q \quad \text{(Equation T2)}$$

$$K = P_{t|t-1} H^T (H P_{t|t-1} H^T + R) \quad \text{(Equation T3)}$$

$$P_{t|t} = (I - KH) P_{t|t-1} \quad \text{(Equation T4)}$$

$$X_{t|t} = X_{t|t-1} + K(HI - HX_{t|t-1}) \quad \text{(Equation T5)}$$

Note that the subscript notation above, for example, such as "t|t−1" refers to determining a value of at a time t conditioned on the measurement at a time of "t−1". Similarly, "t|t" refers to, for example, determining an estimate at a time "t" conditioned on a measurement of time "t".

The current HI determined, for example, using other techniques described herein, may be input into Equation T5 to obtain a projected value for HI_est, the best estimate of the current HI. To project the expect HI "n" units of time into the future, input the number of units of time "dt" into Φ (as described above), and use the state update equation (Equation T1) where now Equation T1 becomes: $X_{t+dt|t} = \Phi X_{t|t}$. This allows the best prediction of HI_est any number of units of time into the future where HI_est is desired. It should be noted that as set forth above, the linear matrix operation such as Φ X is equivalent to an integration from t to dt of the state of X, where X represents the vector of HI values set forth above.

Different values may be selected for initial conditions in accordance with each embodiment. For example, an initial value for P representing the covariance may be (1/mean time value between failures). An embodiment may use any one of a variety of different techniques to select an initial value for P. Additionally, since P converges rapidly to an appropriate value and the time between data acquisitions is small in comparison to the mean failure time, selecting a particularly good initial value for P may not be as important as other initial conditions. A value for σ may be selecting in accordance with apriori information, such as manufacturer's data on the mean time between component parts' expected failure time. For example, for a transmission, the mean failure time may be approximately 20,000 hours. The spectral density may be set to $(1/20,000)^2$. It should be noted that the failure rates may be generally characterized as an exponential type of distribution. The mean time between expected failures is a rate, and the variance is that rate to the second power. R may also be determined using apriori information, such as manufacturer's data, for example, an estimated HI variance of manufacturer's data of a healthy component. Q may be characterized as the mean time between failures and dt (delta change in time between readings). As the value of dt increases, Q increases by the third power.

Input data used in the foregoing trending equations may be retrieved from collected data, for example, as may be stored in the system of FIG. 1.

In determining HIs, for example, as in connection with the system of FIG. 1 for particular components, HIs may be derived using one or more CIs. In calculating CIs, data acquisitions may occur by recording observed data values using sensors that monitor different components. There may be a need for estimating data used in connection with CI calculations, for example, in instances in which there may be too little or no observed empirical. For example, in connection with a power train, there may be a need to obtain estimated data, for example, for each bearing, shaft and gear within the power train to calculate CIs. However, insufficient empirical data may exist in connection with gear or bearing related measurements, such as, for example, those in connection with a gear or bearing related measurements, such as, for example, those in connection with a gear or bearing fault due to the rare occurrence of such events. In such instances, mean and threshold values may be derived using other techniques.

A CI may indicate a level of transmission error, for example, in which transmission error is a measure of the change in gear rigidity and spacing. Modeling transmission error may allow one to gauge CI sensitivity and derive threshold and mean values indicative of gear/bearing failure. This transmission error modeling may be referred to as dynamic analysis. What will now be described is a technique that may be used to model a gears to obtain such estimated values. By modeling each gear pair as a damped spring model with the contact line between the gears, transmission error may be estimated. It should be noted that this model uses two degrees of freedom or movement. Other systems may use other models which may be more complex having more degrees of freedom. However, for the purposes of estimating values, this model has proven accurate in obtaining estimates. Other embodiments may use other models in estimating values for use in a system such as that of FIG. 1.

Figure 30:
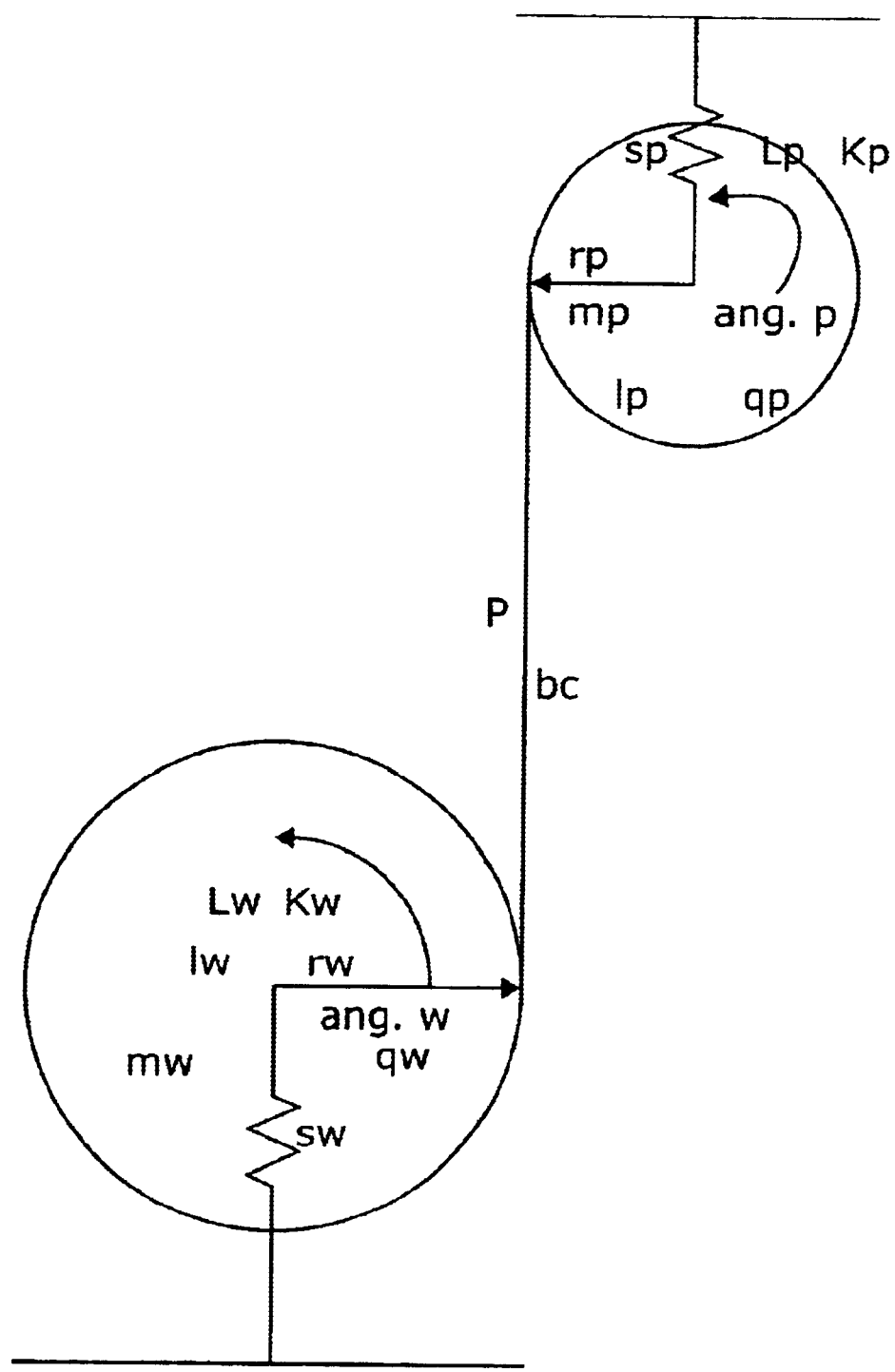
FIG. 30 is an example of an embodiment of a gear model.

Referring now to FIG. 30, shown is an example of an illustration of a pair of gears for which a model will now be described. A force P at the contact gives linear and torsional response to each of the 2 gears for a total of four responses as indicated in FIG. 30. The relative movement d at P is the sum of the 4 responses together with the contact deflection due to the contact stiffness $s_c$ and the damping coefficient $b_c$. This may be represented as:

$$d = P(1/sp + j\omega bp - mp\omega^2 + rp^2/kp + j\omega qp - Ip\omega^2 + 1/sw + j\omega bw - mw\omega^2 + rw^2/kw + j\omega qw - Iw\omega^2 + 1/sc + j\omega bc) \quad \text{EQUATION G1}$$

in which:
sp is the linear stiffness of the pinion;
j is the square root of −1;

ω is the angular rate that may be obtained from the configuration file (e.g., shaft rpm*60*2π to obtain radians per second for the pinion driving the wheel);
bp is the linear damping coefficient of the pinion;
mp is the mass of the pinion;
rp is the radius of the pinion;
kp is the angular effective stiffness of the pinion;
qp is the angular damping coefficient of the pinion;
Ip is the angular effective mass of the pinion;
sw is the linear stiffness of the wheel;
bw is the linear damping coefficient of the wheel;
mw is the mass of the wheel;
rp is the radius of the pinion;
kw is the angular effective stiffness of the wheel;
qw is the angular damping coefficient of the wheel;
Iw is the angular effective mass of the wheel;
sc is the linear stiffness of the contact patch where the two gears come into contact;
bc is the linear damping coefficient of the contact patch;

It should be noted that values for the above-referenced variables on the rights hand side of EQUATION G1 above, except for P (described below), may be obtained using manufacturer's specifications for a particular arrangement used in an embodiment. An embodiment may include quantities for the above-referenced variables in units, for example, such as stiffness in units of force/distance (e.g., newtons/meter), mass in kg units, and the like.

The relative movement, d, is the T.E., so from d, the above-referenced equation can be solved for P, the tooth force. Deflection is the force (input torque divided by the pinion base radius)*the elastic deflection of the shafts, which may be used in estimating P represented as:

$$P=(1/kp*rp)+(1/sp)+(1/sw)+(1/kwrw) \quad \text{EQUATION G2}$$

where the variables are as described above in connection with EQUATION G1. Using the above estimate for P with EQUATION G1, the displacement, such as a vibration transmitted through the bearing housing and transmission case (which acts an additional transfer function), may be determined.

Referring again to FIG. 30, shown is an example of an illustration of the gear model and the different variables used in connection with EQUATION G1 and G2. Lp may represent the longitudinal stiffness of the pinion and Lw may represent the longitudinal stiffness of the wheel. It should be noted that these elements may not be included in an embodiment using the two degrees of freedom model.

Bearings may also be modeled to obtain estimates of fault conditions in instances where there is little or no empirical data available. With bearings, a periodic impulse is of interest. The impulse is the result of a bearing rolling over a pit or spall on the inner or outer bearing race. The intensity of the impulse on the bearing surface is a function of the angle relative to the fault, which may be represented as, for example, described in the Stribeck equation in a book by T. A. Harris, 1966, *Rolling Bearing Analysis*. New York: John Wiley p 148 as:

$$q(\theta)=q_0[1-(1/2\epsilon)(1-\cos\theta)]^n \quad \text{EQUATION B1}$$

where n=3/2 for ball bearings and 10/9 for rolling elements bearing, $\epsilon<0.5$, and θ is less than π/2 in accordance with values specified in this particular text for the different bearings used in the above-referenced Stribeck equation represented as in EQUATION B1.

An impulse in a solid surface has an exponential decay constant, which may be taken into account, along with a periodic system due to rotation of the shaft. The bearing model may then be represented as a quantity, "s", which is the multiplication of the impulse, "imp" below, the impulse intensity, "q(θ)" as may be determined above, the period shaft rotation, which is "cos(θ)" below, all convoluted by the exponential decay of the material and represented as:

$$s = [\text{imp} \times q(\theta) \times \cos \theta] \otimes \exp(T/t) \quad \text{EQUATION B2}$$

where T is the exponential decay and t is the time. It should be noted that "T" varies with the material of the solid surface. "exp(T/t)" may be obtained, for example, using a modal hammer, to generate the decay response experimentally. An embodiment may also obtain this value using other information as may be supplied in accordance with manufacturer's information. The value of "t" may be a vector of times starting with the first time sample and extending to the end of the simulation. T is generally small, so the expression "exp(T/t)" approaches zero rapidly even using a high sampling rate.

"imp" is the impulse train that may be represented as the shaft rate*bearing frequncy ratio*sampling rate for the simulation period.

"s" is the simulated signal that may be used in determining a spectrum, "S", where "S=fft(s)", the Fourier transform of s into the frequency domain from the time domain. As described in more detail in following paragraphs, in determining a CI in connection with the bearing model signal "s" having spectrum "S", for example, the Power Spectral Density of S at a bearing passing frequency may be used as a CI. Additionally, for example, other CI values may be obtained, such as in connection with the CI algorithm comparing the spectrum "S" to those associated with transmission error in connection with a normal distribution using the PDF/CDF CI algorithms that may be generally described as hypothesis testing techniques providing a measure of difference with regard whether the spectrum is normally distributed.

It should be noted that, as described elsewhere herein in connection with gear models, values may be used in the foregoing equations in connection with simulating various fault conditions and severity levels. The particular values may be determined in accordance with what small amount of observed data or manufacturer's data may be available. For example, in accordance with observed values, an impulse value of 0.02 for the impulse, "imp", may correspond to a fairly severe fault condition. Values ranging from 0.001 to 0.03, for example, may be used to delimit the range of "imp" values used in simulations.

Following is an example of estimated data using the foregoing equations for a bearing having the following configurations:

Rpm=287.1
Roller diameter=0.25
Pitch diameter=1.4171
Contact angle=0
Number of elements=10

Inner Race Fault

Figure 31:
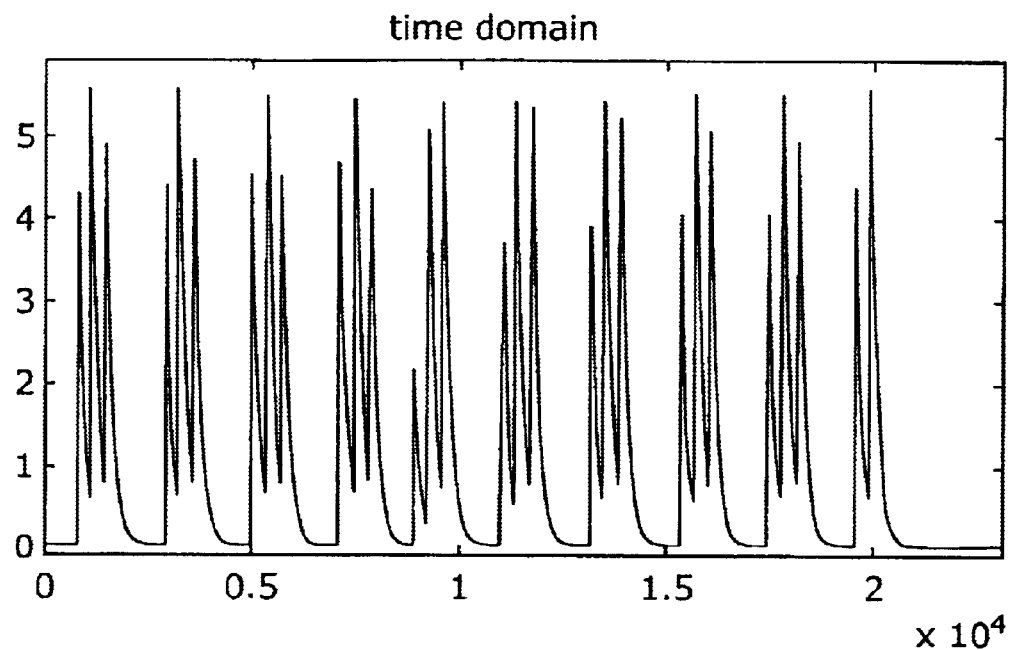
FIG. 31 is a graphical representation of an estimated signal having an inner bearing fault.
Figure 32:
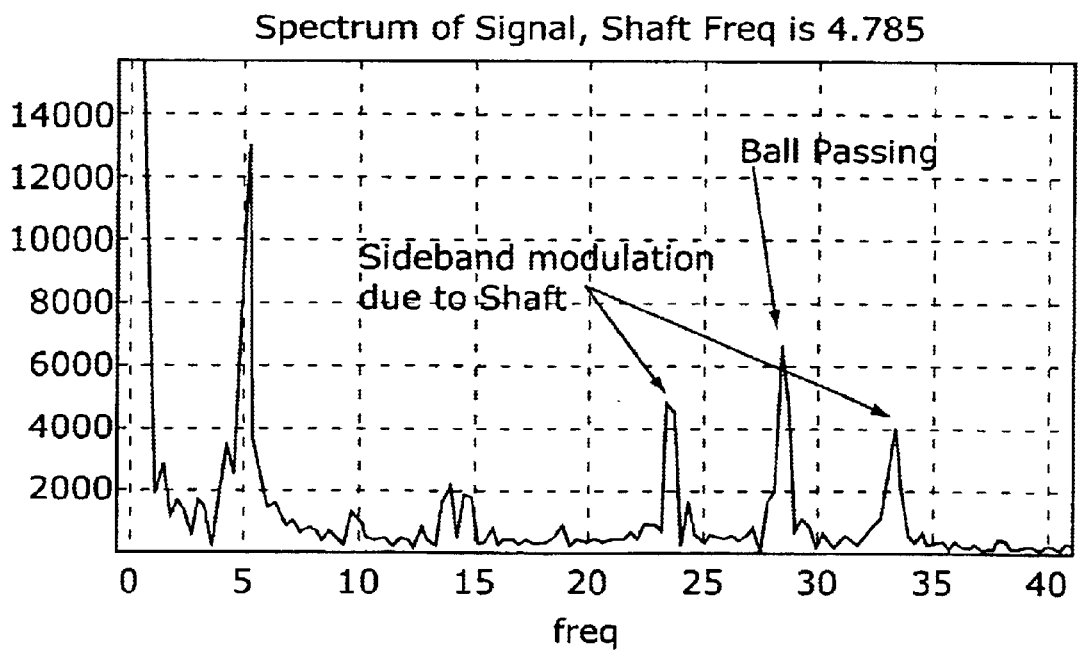
FIG. 32 is a graphical representation of the signal of FIG. 31 as a frequency spectrum.

Referring now to FIG. 31, shown is an example of a graphical representation of the signal for the foregoing configuration when there is some type of bearing fault as estimated using the foregoing equations EQUATION B1 and B2. FIG. 32 represents the estimated spectrum "S" as may be determined using EQUATION B2 above.

It should be noted that for bearings, there may be three types of faults, for example, estimated using the foregoing equations. There may be an inner race fault, an outer race fault or a roller element fault. Localized bearing faults induce an excitation which can be modeled as an impulse train, expressed as imp in the above equation. This impulse "imp" corresponds to the passing of the rolling elements of the fault. Assuming a constant inner ring rotation speed, the impulse train is periodic and the periodicity depends on the fault location.

For outer race faults, the bearing frequency ratio, $f_{d,or}$ may be represented as:

$$f_{d,or} = \frac{N}{2}\left(1 - \frac{d_b}{d_m}\cos(\alpha)\right)(f_{ir} - f_{or}) \quad \text{EQUATION B3}$$

where:
"$d_b$" represents the roller diameter,
"$d_m$" represents the pitch diameter,
"$\alpha$"=2π*frequency, $f_d$;
"$f_{ir}$" is the rotation frequency of the inner race (e.g. shaft rate), and
"$f_{or}$" the rotation frequency of the outer race (if fixed=0).

For inner race faults, the bearing frequency ratio, $f_{d,ir}$ may be represented as:

$$f_{d,ir} = \frac{N}{2}\left(1 + \frac{d_b}{d_m}\cos(\alpha)\right)(f_{ir} - f_{or}) \quad \text{EQUATION B4}$$

Replacing α with $2\pi f_d$, the time response is f(t). This substitution may be performed as the initial value of α is based on an angle and not a function of time. In a simulation, there is a time dependent response as expressed using f(t).

The radial load applied to the bearing is not constant and results in a load distribution, which is a function of angular position. If the defect is on the outer race, the amplitude of the impulse is constant because the fault location is not time varying. For an inner race fault, the amplitude with respect to angular position. The function is:

$$q(\theta) = \begin{cases} q_o(1 - 1/2\varepsilon(1 - \cos\theta))^n \\ 0 \text{ elsewhere} \end{cases} \text{ for } |\theta| \leq \theta_{max} \quad \text{EQUATION B5}$$

q(t)=q(2πf(θ)). This quantity q(t) is amplitude at a particular time, or q(theta) representing the amplitude at a particular angle. Amplitude modulation takes into account the distance from the fault to the sensor. For outer race fault, the quantity cos (θ) is constant (1), for inner race fault, it is the cosine function, noted as "cos (θ)" in the above equation.

For a linear system, the vibrations at a given frequency may be specified by the amplitude and phase of the response and the time constant of the exponential decay. As the angle, θ above, changes, the impulse response, h(t), and the transfer function H(f) also change due to the changing transmission path and angle of the applied impulse. It is assumed that the exponential decays is independent of the angle θ, so that the response measured at a transducer due to an impluse applied to the bearing at the location θ is characterized by an amplitude which is a function of θ.

The impulse response function h(t) and the transfer function H(f) may be replaced by a function a(θ) giving the amplitude and sign of the transfer function H(f) at each angle theta and by the exponential decay of a unit impulse, (e(t)). For an inner race defect, rotating at the shaft frequency fs, the instantanous amplitude of the transfer function between the defect and the transducer as a function of time, a(t) may be obtained by substituting $2\pi*fs*t$ for theta. Note that a(t) is periodic. At $\theta=0$ relative to the defect and transducer, a(t) has its maximum value. At $\theta=\pi$, a(t) should be a minimum because the distance form the defect to the transducer is a minimum. Additionally, the sign is negative because the impulse is in the opposite direction. Because of these properties, the cos(t) may be used for the function a(t).

The impulse train is exponentially decaying. The decay of a unit impulse can be defined by:

$$e(t)=\exp(-t/T_e) \quad \text{EQUATION B6}$$

for t>0, where $T_e$ is the time constant of decay.
The bearing fault model is then:

$$v(t)=[imp(t)q(t)a(t)]*e(t) \quad \text{EQUATION B7}$$

where:
  imp(t), which is the impulse over a time $t,=2\pi*$shaft rat,*time*bearing frequency ratio, as may be determined using EQUATIONS B3 and B4 above;
  a(t) is the $\cos(\theta)$ for an inner race, which is 1 for an outer race, where $\cos(\theta)=0$, where $\theta$ is time varying;
  and q(t) and e(t) are as described above.

An embodiment may include a signal associated at the sensor for gear and bearing noise combined from the bearing and the gear model may be represented as:

$$s(t)=[d(t)f(t)q(t)a(t)]*e(t)*h(t) \quad \text{EQUATION B8}$$

where:
  h(t) is the frequency response of the gear case, as may be determined, for example, using an estimate produced with linear predictive coding (LPC) techniques or with a modal hammer analysis;
  d(t) is the signal associated with gear/shaft T.E. as may be determined using the gear model EQUATION G1;
  and other variables are as described elsewhere herein.

The frequency spectrum of signals representing a combined bearing and gear model from EQUATION B8 may be represented as:

$$S(f)=[D(f)*F(f)*Q(f)*A(f)]E(f)H(f) \quad \text{EQUATION B9}$$

As described elsewhere herein, healthy data, such as may be obtained using manufacturer's information, may be used in determining different values, such as those in connection with stiffnesses for gear simulation, amplitude and exponential decay for bearing faults. In terms of generating fault data, since these systems are linear, the following may be defined:

For gear faults indicative of a crack, a reduction in the stiffness for a tooth (e.g. 50 and 20 percent of normal) may be used in estimating median and high fault values. Additionally, these values may be varied, for example, using the Monte Carlo simulation to quantify variance.

For shaft misalignment, shaft alignment within the model may be varied to estimate mean fault values.

For gear spalling faults, the "size" of an impulse may be determined through trial and error, and by comparing simulation values with any limited observed fault data previously collected.

For bearing fault models, which are spalling faults, the size of an impulse, indicative of a fault, with known bearing faults, may be determined similarly as with gear spalling faults.

Sensitivity analysis may be performed, for example using range of different input values for the different parameters, to provide for increasing the effectiveness of fault detection techniques, for example, as described and used herein. For example, an embodiment may be better able to simulate a family of bearing faults to tailor a particular CI algorithm to be sensitive to that particular fault.

Using the foregoing, the modulated transmission error of a gear mesh, for example, which is a signal may be simulated or estimated. This signal may subsequently be processed using any one or more of a variety of CI algorithms such that estimates for the mean and threshold values can then be derived for fault conditions. (It is assumed that the stiffness and torque are known apriori). Parameter values used in the above equations corresponding to a healthy gear, for example, as may be specified using manufacturer's data, may be modified to estimate parameter values in connection with different types of faults being simulated. By modifying these parameter values, different output values may be determined corresponding to different fault conditions.

For example, known values for stiffness, masses, and the like used in EQUATION G1 may be varied. A cracked gear tooth may be simulated by making the stiffness time varying. The contact pitch may be varied with time in simulating a shaft alignment fault. A modulated input pulse on d may be used in simulating a spall on a gear tooth. Different parameter values may be used in connection with specifying different degrees of fault severity, such as alarm levels and warning levels. A particular parameter value, such as a tooth stiffness of 70% of the normal manufacturer's specified stiffness, may be used in simulating warning levels. A value of 20% of the normal manufacturer's specified stiffness may be used in simulating alarm levels. The particular values may be determined in accordance with comparing calculated values with the characteristics of real CI data on any few real faults collected.

While the invention has been disclosed in connection with the preferred embodiments shown and described in detail, various modifications and improvements thereon will become readily apparent to those skilled in the art. Accordingly, the spirit and scope of the present invention is to be limited only by the following claims.

What is claimed is:

1. A method for determining a health indicator associated with a component, comprising:
  determining a plurality of health classifications;
  determining at least one condition indicator quantifying a characteristic of said component;
  determining a probability associated with each of said health classifications, said probability being an estimation that said component is of a particular health classification given said at least one condition indicator; and
  determining, for a given set of observed values, which of said plurality of health classifications is associated with said component using said probabilities associated with said health classifications,
  wherein said determining at least one condition indicator, said determining a probability, and said determining which of said health classifications is associated with said component, are performed upon two of said plurality of health classifications, and
  wherein, if a determination is made that a first of said health classifications is not associated with said component, repeating said determining at least one condition indicator, said determining a probability, and said determining which of said health classifications is associated with said component using two other health classifications.

2. The method of claim 1, further comprising:

storing previously observed and calculated data associated with said component; and using a portion of said previously observed and calculated data to determine said probability associated with said each health classification.

3. The method of claim 1, further comprising:

obtaining data estimates using models of said component; and using said data estimates to determine said probability associated with said each health classification.

4. A method for determining a health indicator associated with a component, comprising:

determining a plurality of health classifications;

determining at least one condition indicator quantifying a characteristic of said component;

determining a probability associated with each of said health classifications, said probability being an estimation that said component is of a particular health classification given said at least one condition indicator;

determining, for a given set of observed values, which of said plurality of health classifications is associated with said component using said probabilities associated with said health classifications;

determining a threshold using a ratio of a portion of said probabilities;

calculating a current quantity associated with said component using said observed values; and comparing said current quantity to said ratio to determine which of said health classifications is associated with said component.

5. The method of claim 4, wherein said calculating said current quantity further comprises:

determining a transformation matrix maximizing a distance between two of said plurality of health classifications;

determining a covariance matrix for each of said health classifications using said at least one condition indicator and said observed values; and determining said current quantity in accordance with said covariance matrices, said transformation matrix and said observed values.

6. The method of claim 5, wherein, for two of said plurality of health classifications, said current quantity, h(X), may be represented as:

$$h(X) = \tfrac{1}{2} Y^T \Lambda^{-1} Y - ((-K^{-1}L)^T) Y + (-\tfrac{1}{2} L^T K^{-1} L - \tfrac{1}{2} \ln|K| - \ln P_2/P_1)$$

wherein,

X represents said at least one conditional indicator forming a vector of individual conditional indicator values;

Y represents $\Lambda^{-1/2} \Phi^T X$;

$\Lambda$ represents $(I - K^{-1})^{-1}$, diagonal matrix of eigenvalues of X using a characteristic equation of $\Sigma \Phi = \Phi \Lambda$, $\Phi^T \Phi =$ identity matrix;

$\Phi$ represents an nxn matrix of eigenvectors, $\Phi \ldots \Phi n$, of X using said characteristic equation;

I represents $A^T \Sigma 1 A$;

K represents $A^T \Sigma 2 A$;

L represents $A^T (M2 - M1)$;

P2 represents an aposteriori probability of a first of said two health classifications given X;

P1 represents an aposteriori probability of a second of said two health classifications given X;

A represents said transformation matrix maximizing a distance between distributions of said two health classifications represented as $\Lambda^{-1/2} \Phi^T$;

$\Sigma 1$ represents a covariance matrix of said first health classification having a vector of expected values M1; and $\Sigma 2$ represents a covariance matrix of said second health classification having a vector of expected values M2.

7. A method for determining a health status of a component comprising:

selecting a plurality of condition indicators having a value and each having a corresponding weighting factor, and at least one threshold value defining at least two health classifications;

determining a contribution to a health indicator for each of said condition indicators, wherein said determining further comprises, for each of said plurality of indicators:

determining which of said at least two classifications said value of said each condition indicator belongs; and determining said contribution to said health indicator by said each condition indicator in accordance with a selected one of said at least two classifications and said weighted factor; and determining said health indicator according to all contributions by each of said condition indicator values.

8. The method of claim 7, wherein first, second and third classifications are associated with each of said condition indicators formed by two threshold values, and the method further comprises:

determining that said contribution to said health indicator for a first of said condition indicators is zero if said value of said condition indicator is in said first classification;

determining that said contribution to said health indicator is a first multiple of said weighting factor if said value of said condition indicator is in said second classification; and determining that said contribution to said health indicator is a second multiple of said weighting factor if said value of said condition indicator is in said third classification.

9. The method of claim 8, where the two threshold values are alarm level and warning level.

10. A computer program product executed on a processor for determining a health indicator associated with a component, comprising machine executable code for determining a plurality of health classifications;

determining at least one condition indicator quantifying a characteristic of said component;

determining a probability associated with each of said health classifications, said probability being an estimation that said component is of a particular health classification given said at least one condition indicator; and determining, for a given set of observed values, which of said plurality of health classifications is associated with said component using said probabilities associated with said health classifications, wherein machine executable code for determining at least one condition indicator, determining a probability, and determining which of said health classifications is associated with said component, are performed upon two of said plurality of health classifications, and the computer program product further includes machine executable code, wherein, if a determination is made that a first of said health classifications is not associated with said component, for repeatedly determining at least one condition indicator, repeatedly determining a probability, and repeatedly determining which of said health classifications is associated with said component using two other health classifications.

11. The computer program product of claim 10, further comprising machine executable code for:
   storing previously observed and calculated data associated with said component; and
   using a portion of said previously observed and calculated data to determine said probability associated with each health classification.

12. The computer program product of claim 10, further comprising machine executable code for:
   obtaining data estimates using models of said component; and
   using said data estimates to determine said probability associated with said each health classification.

13. A computer program product executed on a processor for determining a health indicator associated with a component, comprising machine executable code for
   determining a plurality of health classifications;
   determining at least one condition indicator quantifying a characteristic of said component;
   determining a probability associated with each of said health classifications, said probability being an estimation that said component is of a particular health classification given said at least one condition indicator;
   determining, for a given set of observed values, which of said plurality of health classifications is associated with said component using said probabilities associated with said health classifications,
   determining a threshold using a ratio of a portion of said probabilities;
   calculating a current quantity associated with said component using said observed values; and
   comparing said current quantity to said ratio to determine which of said health classifications is associated with said component.

14. The computer program product of claim 13, wherein said machine executable code for calculating said current quantity further comprises machine executable code for:
   determining a transformation matrix maximizing a distance between two of said plurality of health classifications;
   determining a covariance matrix for each of said health classifications using said at least one condition indicator and said observed values; and
   determining said current quantity in accordance with said covariance matrices, said transformation matrix and said observed values.

15. The computer program product of claim 14, wherein, for two of said plurality of health classifications, said current quantity, h(X), may be represented as:

$$h(X) = \tfrac{1}{2} Y^T \Lambda^{-1} Y - ((-K^{-1}L)^T) Y + (-\tfrac{1}{2} L^T K^{-1} L - \tfrac{1}{2} \ln|K| - \ln P_2/P_1)$$

wherein,

X represents said at least one conditional indicator forming a vector of individual conditional indicator values;

Y represents $\Lambda^{-1/2} \Phi^T X$;

$\Lambda$ represents $(I-K^{-1})^{-1}$, diagonal matrix of eigenvalues of X using a characteristic equation of $\Sigma\Phi = \Phi\Lambda$, $\Phi^T\Phi =$ identity matrix;

$\Phi$ represents an nxn matrix of eigenvectors, $\Phi 1 \ldots \Phi n$, of X using said characteristic equation;

I represents $A^T \Sigma 1 A$;

K represents $A^T \Sigma 2 A$;

L represents $A^T(M2-M1)$;

P2 represents an aposteriori probability of a first of said two health classifications given X;

P1 represents an aposteriori probability of a second of said two health classifications given X;

A represents said transformation matrix maximizing a distance between distributions of said two health classifications represented as $\Lambda^{-1/2} \Phi^T$;

$\Sigma 1$ represents a covariance matrix of said first health classification having a vector of expected values M1; and $\Sigma 2$ represents a covariance matrix of said second health classification having a vector of expected values M2.

16. A computer program product executed on a processor for determining a health status of a component comprising machine executable code for:
   selecting a plurality of condition indicators having a value and each having a corresponding weighting factor, and at least one threshold value defining at least two health classifications;
   determining a contribution to a health indicator for each of said condition indicators, wherein said machine executable code for determining further comprises, for each of said plurality of indicators, machine executable code for:
      determining which of said at least two classifications said value of said each condition indicator belongs; and
      determining said contribution to said health indicator by said each condition indicator in accordance with a selected one of said at least two classifications and said weighted factor; and
   determining said health indicator according to all contributions by each of said condition indicator values.

17. The computer program product of claim 16, wherein first second and third classification are associated with each of said condition indicators formed by two threshold values, and the computer program product further comprises machine executable code for:
   determining that said contribution to said health indicator for a first of said condition indicators is zero if said condition indicator is in said first classification;
   determining that said contribution to said health indicator is a first multiple of said weighting factor if said condition indicator is in said second classification; and
   determining that said contribution to said health indicator is a second multiple of said weighting factor if said condition indicator is in said third classification.

18. The computer program product of claim 17, where the two threshold values are alarm level and warning level.

* * * * *

UNITED STATES PATENT AND TRADEMARK OFFICE
CERTIFICATE OF CORRECTION

| | |
|---|---|
| PATENT NO. | : 6,728,658 B1 |
| APPLICATION NO. | : 10/011787 |
| DATED | : April 27, 2004 |
| INVENTOR(S) | : Eric Robert Bechhoefer |

It is certified that error appears in the above-identified patent and that said Letters Patent is hereby corrected as shown below:

Column 40, line 47, "classification" should read --classifications--;

Column 40, line 52, after "if said" insert --value of said--;

Column 40, line 55, after "if said" insert --value of said--;

Column 40, line 58, after "if said" insert --value of said--.

Signed and Sealed this

Twenty-fifth Day of September, 2007

JON W. DUDAS
*Director of the United States Patent and Trademark Office*